(12) United States Patent
Petyaev

(10) Patent No.: US 9,737,602 B2
(45) Date of Patent: Aug. 22, 2017

(54) CAROTENOID PARTICLES AND USES THEREOF

(71) Applicant: IP SCIENCE LIMITED, Great Shelford (GB)

(72) Inventor: Ivan Petyaev, Cambridge (GB)

(73) Assignee: IP SCIENCE LIMITED, Cambridge (GB)

( * ) Notice: Subject to any disclaimer, the term of this patent is extended or adjusted under 35 U.S.C. 154(b) by 0 days.

(21) Appl. No.: 15/225,611

(22) Filed: Aug. 1, 2016

(65) Prior Publication Data

US 2017/0049893 A1 Feb. 23, 2017

Related U.S. Application Data

(63) Continuation of application No. 13/982,910, filed as application No. PCT/GB2012/000075 on Jan. 25, 2012, now abandoned.

(30) Foreign Application Priority Data

Jan. 31, 2011 (GB) .................................. 1101669.8

(51) Int. Cl.
*A61K 31/366* (2006.01)
*A61K 31/01* (2006.01)
(Continued)

(52) U.S. Cl.
CPC ............ *A61K 47/06* (2013.01); *A23L 33/105* (2016.08); *A61K 9/0053* (2013.01);
(Continued)

(58) Field of Classification Search
None
See application file for complete search history.

(56) References Cited

U.S. PATENT DOCUMENTS 3,081,171 A * 3/1963 Reiners ................. C07C 403/24
426/547
4,444,784 A * 4/1984 Hoffman ............... C07D 309/30
514/460

(Continued)

FOREIGN PATENT DOCUMENTS

CN 1739523 A * 3/2006
CN 1739524 3/2006
(Continued)

OTHER PUBLICATIONS

Xu, Xiaoying, et al. "Solubilization and stabilization of carotenoids using micelles: delivery of lycopene to cells in culture." Lipids 34.10 (1999): 1031-1036.*

(Continued)

*Primary Examiner* — Bethany Barham
*Assistant Examiner* — Peter Anthopolos
(74) *Attorney, Agent, or Firm* — Nixon & Vanderhye PC

(57) ABSTRACT

This invention relates to the incorporation of bioactive cargo molecules into particles with carotenoids, such as lycopene. The incorporation of a cargo molecule into a carotenoid particle may for example increase the bioavailability of the cargo molecule in the bloodstream compared to other delivery systems. Carotenoid particles as described herein may be useful in the formulation of therapeutic and nutritional compounds for oral administration to individuals.

20 Claims, 8 Drawing Sheets

(51) Int. Cl.
| | |
|---|---|
| A61K 8/55 | (2006.01) |
| A61K 9/51 | (2006.01) |
| A61K 47/06 | (2006.01) |
| A61K 9/107 | (2006.01) |
| A61K 31/355 | (2006.01) |
| A61K 9/14 | (2006.01) |
| A23L 33/105 | (2016.01) |
| A61K 9/00 | (2006.01) |
| A61K 31/05 | (2006.01) |
| A61K 31/351 | (2006.01) |
| A61K 36/00 | (2006.01) |

(52) U.S. Cl.
CPC ............ *A61K 9/1075* (2013.01); *A61K 9/14* (2013.01); *A61K 31/05* (2013.01); *A61K 31/351* (2013.01); *A61K 31/355* (2013.01); *A23V 2002/00* (2013.01); *A61K 36/00* (2013.01)

(56) References Cited

U.S. PATENT DOCUMENTS

| | | |
|---|---|---|
| 7,588,781 B2 | 9/2009 | Bortlik et al. |
| 8,455,004 B2 | 6/2013 | Bortlik et al. |
| 2002/0107292 A1 | 8/2002 | Bortlik et al. |
| 2003/0232095 A1* | 12/2003 | Garti ............... A61K 8/02 424/725 |
| 2005/0106219 A1 | 5/2005 | Bortlik et al. |
| 2007/0071830 A1 | 3/2007 | Bortlik et al. |
| 2009/0123542 A1 | 5/2009 | Bortlik et al. |
| 2009/0162485 A1 | 6/2009 | Schmitt et al. |
| 2013/0337068 A1 | 12/2013 | Petyaev |

FOREIGN PATENT DOCUMENTS

| | | | |
|---|---|---|---|
| EP | 1 839 498 | | 10/2007 |
| IL | WO 2008032327 A2 * | 3/2008 | ........... A61K 9/1075 |
| KR | 20020042218 A * | 6/2002 | |
| WO | 94/13265 | | 6/1994 |
| WO | 01/91588 | | 12/2001 |
| WO | 03/105607 | | 12/2003 |
| WO | 2007/010216 | | 1/2007 |
| WO | 2007/110422 | | 10/2007 |

OTHER PUBLICATIONS

Böhm, Volker, and Roland Bitsch. "Intestinal absorption of lycopene from different matrices and interactions to other carotenoids, the lipid status, and the antioxidant capacity of human plasma." European Journal of Nutrition 38.3 (1999): 118-125.*

Patel, Deepa, and Krutika K. Sawant. "Self micro-emulsifying drug delivery system: formulation development and biopharmaceutical evaluation of lipophilic drugs." Current drug delivery 6.4 (2009): 419-424.*

Kang, Bok Ki, et al. "Development of self-microemulsifying drug delivery systems (SMEDDS) for oral bioavailability enhancement of simvastatin in beagle dogs." International journal of pharmaceutics 274.1 (2004): 65-73.*

Bashmakov et al. "Chlamydia trachomatis growth inhibition and restroration of LDL-receptor level in HepG2 cells treated with mevastatin" *Comparative Hepatology*, 9:3, eight pages (Jan. 2010).

Bashmakov et al. "ApoB-containing lipoproteins promote infectivity of *chlamydial* species in human hepatoma cell line" *World Journal of Hepatology*, 2:74-80 (Feb. 2010).

Caldwell et al. "Purification and partial characterization of the major outer membrane protein of Chlamydia trachomatis" *Infection and Immunity*, 31:1161-1176 (Mar. 1981).

Engelmann et al. "Chronic perivascular inoculation with Chlamydophila pneumoniae results in plaque formation in vivo" *Laboratory Investigation*, 86:467-476 (May 2006).

Frestedt et al. "A whey-protein supplement increases fat loss and spares lean muscle in obese subjects: A randomized human clinical study" *Nutrition & Metabolism*, 5:8, seven pages (Mar. 2008).

Hung et al. "Development and evaluation of emulsion-liposome blends for resveratrol delivery" *Journal of Nanoscience and Nanotechnology*, 6:2950-2958 (Sep.-Oct. 2006).

Morelli et al. "The introduction of the stilbene synthase gene enhances the natural antiradical activity of Lycopersicon esculentum mill." *Molecular and Cellular Biochemistry*, 282:65-73 (Jan. 2006).

Petyaev et al. "Isolation of Chlamydia pneumoniae from serum samples of the patients with acute coronary syndrome" *International Journal of Medical Sciences*, 7:181-190 (Jun. 2010).

Richelle et al. "A food-based formulation provides lycopene with the same bioavailability to humans as that from tomato paste" *Journal of Nutrition*, 132:404-408 (Mar. 2002).

Shor *Chlamydia Atherosclerosis Lesion: Discovery, Diagnosis and Treatment*, Springer-Verlag, London, pp. 1-179 (Nov. 2007).

Tadros "Surfactants" *Kirk-Othmer Encyclopedia of Chemical Technology*, Wiley, Hoboken, NJ, pp. 1-46 (Jul. 2012).

Trivedi et al. "Nanomicellar formulations for sustained drug delivery: Strategies and underlying principles" *Nanomedicine*, 5:485-505 (Apr. 2010).

Xu, et al. "Solubilization and stabilization of carotenoids using micelles: Delivery of lycopene to cells in culture" *Lipids*, 34:1031-1036 (Oct. 1999).

Int'l Search Report for PCT/GB2012/000075, six pages (dated Nov. 2012).

Written Opinion of ISA for PCT/GB2012/000075, 12 pages (dated Jul. 2013).

Int'l Preliminary Report on Patentability for PCT/GB2012/000075, 13 pages (dated Aug. 2013).

Barros et al. "Astaxanthin and peridinin inhibit oxidative damage in $Fe^{2+}$ loaded liposomes: Scavenging oxyradicals or changing membrane permeability?" *Biochemical and Biophysical Research Communications*, 288:225-232 (Oct. 2001).

Junghans et al. "Carotenoid-containing unilamellar liposomes loaded with glutathione: A model to study hydrophobic-hydrophilic antioxidant interaction" *Free Radical Research*, 6:801-808 (Dec. 2000).

Nakagawa et al. "Fusion and molecular aspects of liposomal nanocarriers incorporated with isoprenoids" *IEEE Transactions on Nanobioscience*, 6:219-222 (Sep. 2007).

* cited by examiner

Fig. 1
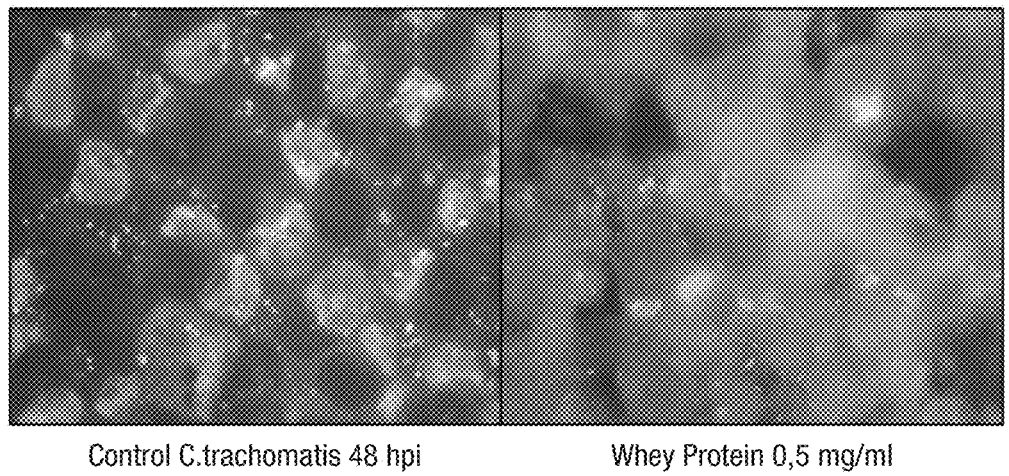
Control C.trachomatis 48 hpi | Whey Protein 0,5 mg/ml
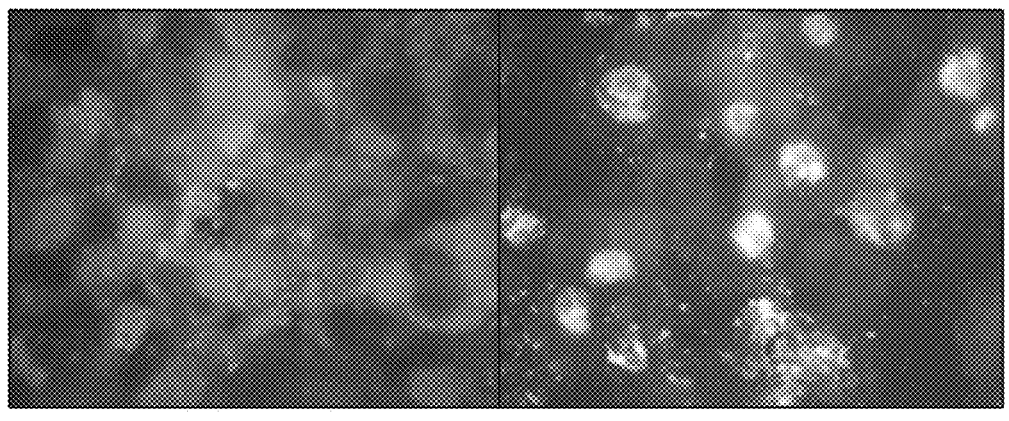
Whey Protein 0,032 mg/ml | Whey Protein 0,016 mg/ml

Fig. 3
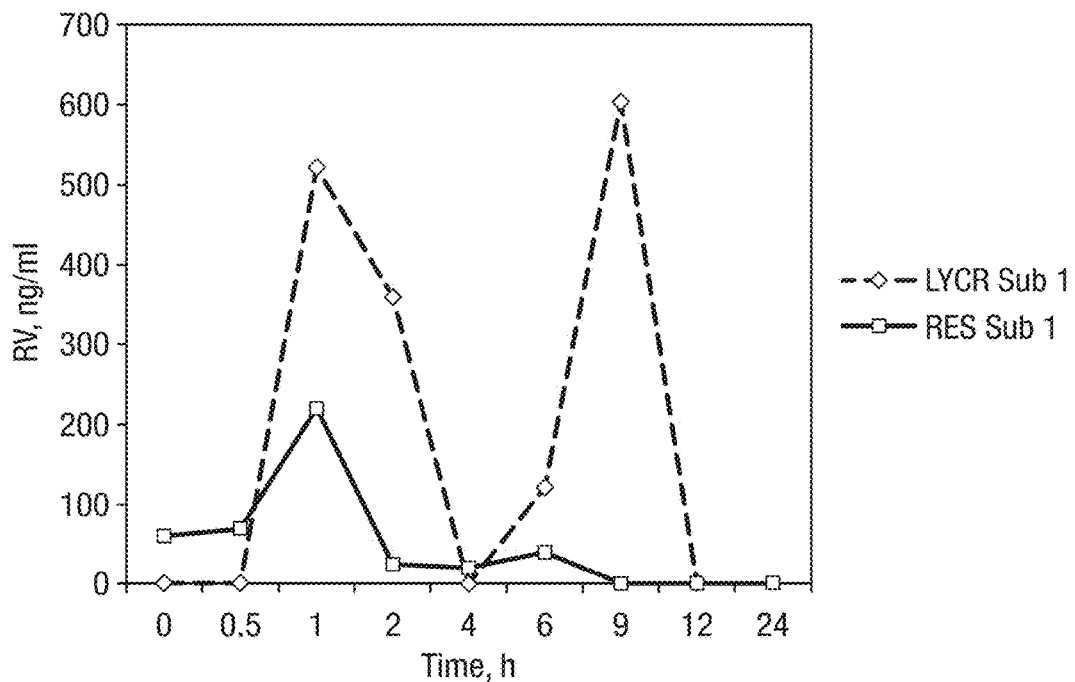
Volunteer 1.
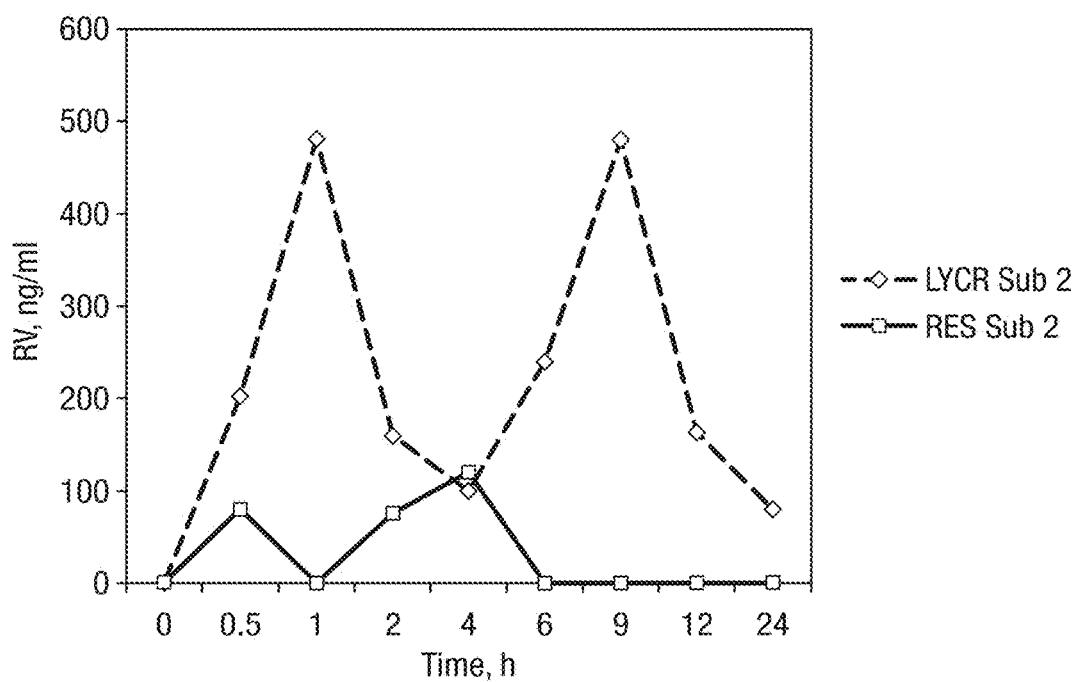
Volunteer 2.

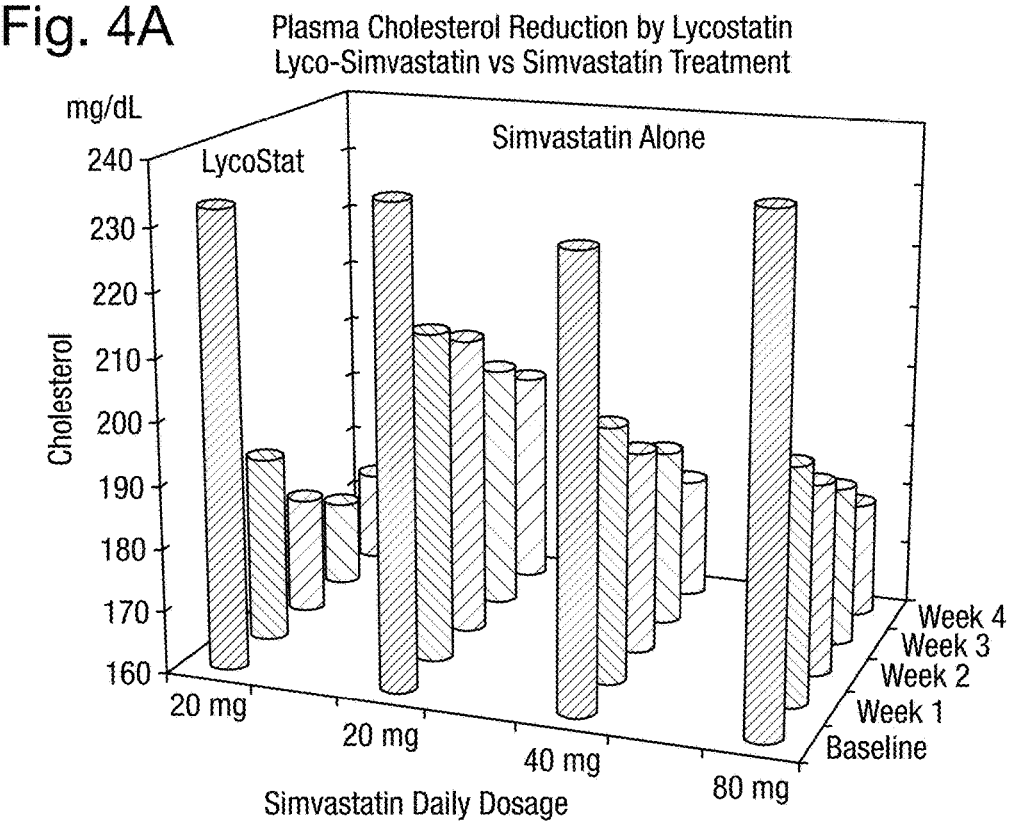
Fig. 4A  Plasma Cholesterol Reduction by Lycostatin
Lyco-Simvastatin vs Simvastatin Treatment
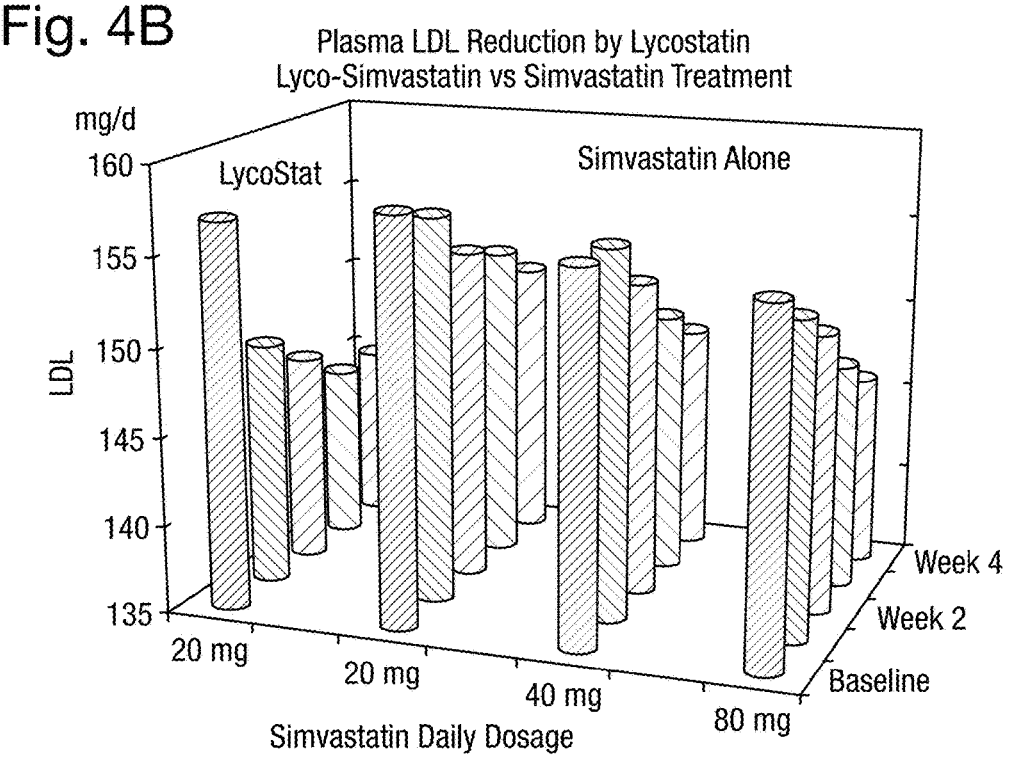
Fig. 4B  Plasma LDL Reduction by Lycostatin
Lyco-Simvastatin vs Simvastatin Treatment

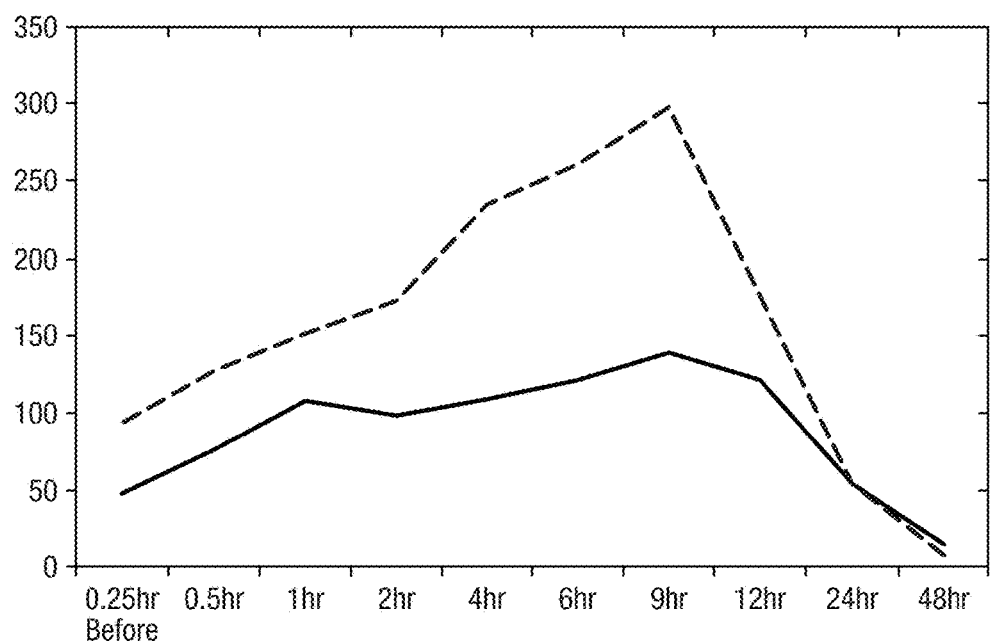
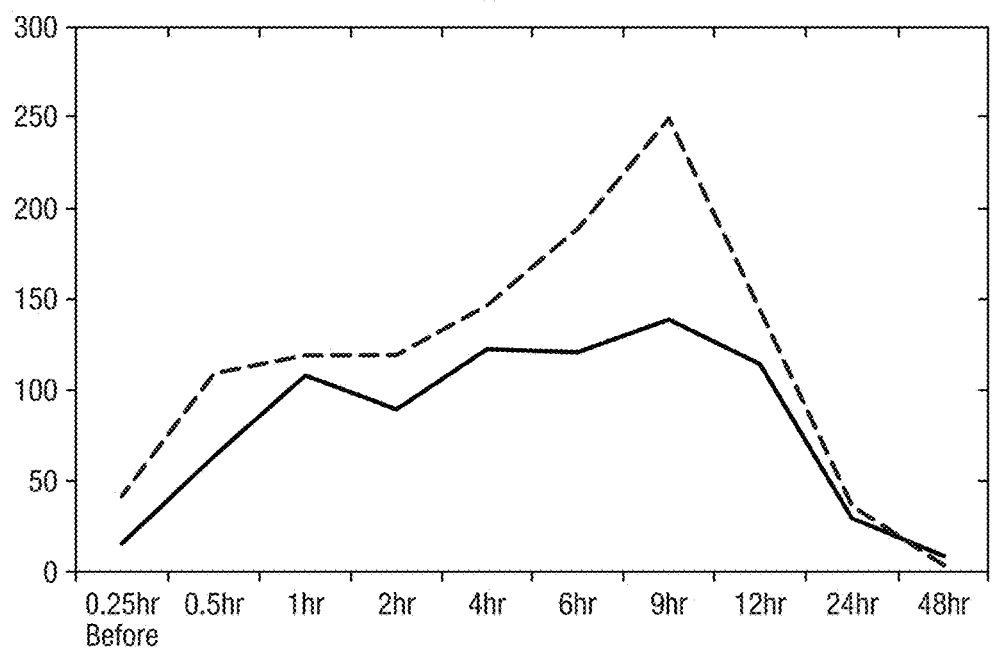

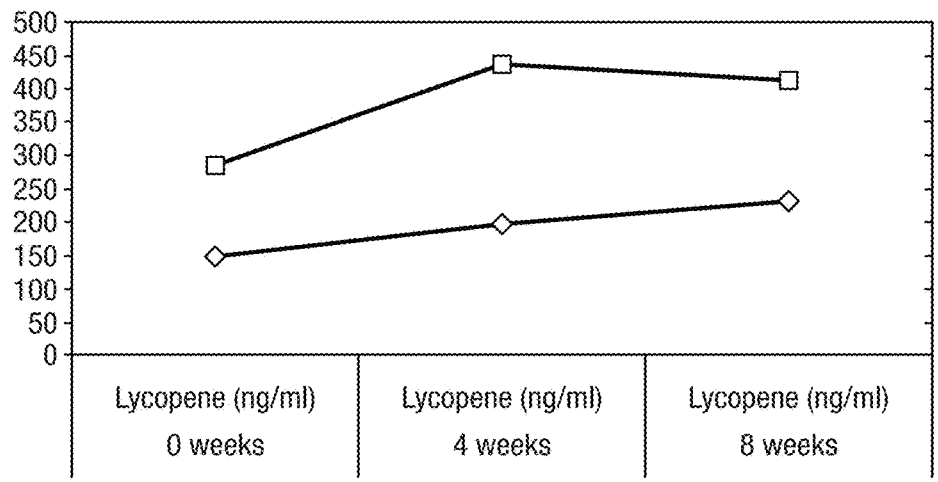
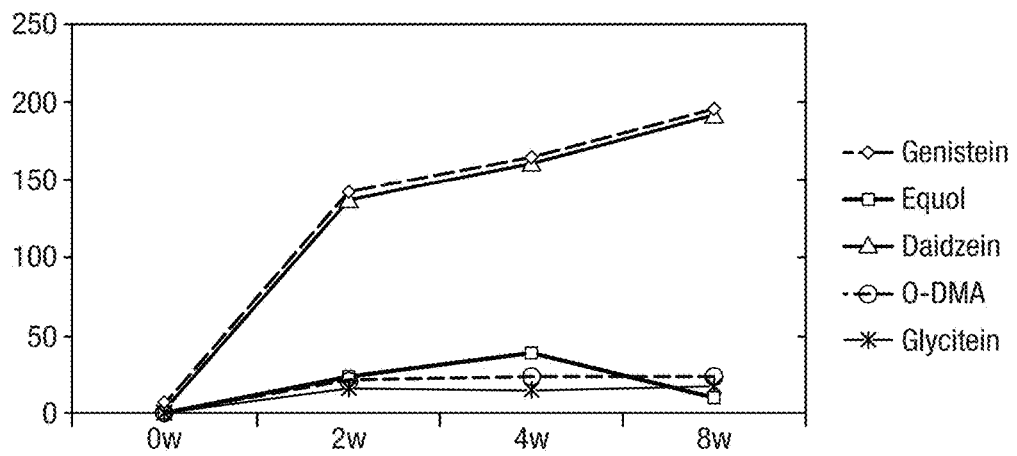

CAROTENOID PARTICLES AND USES THEREOF

This application is a continuation of application Ser. No. 13/982,910, filed Sep. 5, 2013, pending; which is the U.S. national stage of Int'l Application No. PCT/GB2012/000075, filed 25 Jan. 2012; which claims priority benefit of GB Application No. 1101669.8, filed 31 Jan. 2011; the entire contents of each of which are hereby incorporated by reference.

This invention relates to vehicles for the delivery of molecules into the bloodstream of individuals.

Substances which are administered orally, such as pharmaceuticals and dietary supplements, are often modified or damaged, for example by enzymatic degradation, oxidation or stomach acidity, in the gastrointestinal tract. This modification or damage reduces the absorption and subsequent bioavailability of the substance in the blood stream.

Formulation with a carrier may increase the amount of a labile substance which is absorbed in an unmodified or undamaged form, thereby increasing its bioavailability in the bloodstream.

Whey protein has previously been used as a carrier to increase the activity of lycopene (Richelle et al J. Nutr. 132:404-408, 2002; PCT/EP01/06145). Lycopene formulated with a whey protein carrier has been reported to inhibit atherogenic serum abzymes and be useful in the treatment of atherosclerotic conditions (WO2007/010216).

This invention relates to the finding that carotenoids, such as lycopene, may be useful in delivering cargo molecules into the bloodstream. The incorporation of a cargo molecule into a carotenoid particle may lead to increased bioavailability of the cargo molecule in the bloodstream compared to other delivery systems, allowing the dose required to achieve efficacy to be reduced or increasing the efficacy of the same dose. Carotenoid particles may be useful in the formulation of therapeutic and nutritional compounds for oral administration to individuals.

An aspect of the invention provides a population of particles, each particle comprising a carotenoid compound and one or more cargo molecules.

Carotenoids are resistant to enzymatic degradation in the gastrointestinal tract. The incorporation of cargo molecules into carotenoid particles as described herein provides protection from damage and/or modification in the gastrointestinal tract.

In some embodiments, in one or more of the carotenoid particles in the population, the carotenoid compound may form layer, for example an outer layer or interim layer which encapsulates an inner core comprising the one or more cargo molecules (i.e. micelles or reverse micelles). For example, 1% or more, 10% or more, 20% or more, 30% or more or 40% or more of the particles in the population may possess this micelle structure. Up to 100%, up to 95%, up to 90%, up to 80%, up to 70% or up to 60% of the particles in the population may possess this micelle structure. Carotenoid micelles may be soluble, and may for example exist in aqueous solution.

In some embodiments, in one or more of the carotenoid particles in the population, the carotenoid compound may form a matrix into which cargo molecules or their hydrophobic moieties are anchored or embedded (i.e. a non-micelle or composite particle). For example, 1% or more, 10% or more, 20% or more, 30% or more or 40% or more of the particles in the population may possess this composite structure. Up to 100%, up to 95%, up to 90%, up to 80%, up to 70% or up to 60% of the particles in the population may possess this composite structure. Non-micelle particles may exist in a dried form or as suspensions or colloids.

The proportion of particles in a population with micelle or non-micelle structure may be determined using routine techniques.

The carotenoid particles in a population may have uniform or substantially uniform structures (i.e. a homogenous population) or non-uniform or substantially non-uniform structures (i.e. a heterogeneous population).

The carotenoid particles may exist in aggregates or clusters within a population.

The structures adopted by carotenoid particles in a population depend on a number of factors, including the production method, the size, shape and hydrophobicity of the cargo molecule(s), the ratio of carotenoids to cargo molecules, the presence of surfactants, the ratio between the hydrophobic and hydrophilic parts of the cargo molecule(s) and the homogeneity and purity of the cargo molecule(s), especially if the particles contain more than one type of cargo molecule.

Carotenoid compounds are a class of tetraterpenoids which contain long polyene chains. Carotenoids include xanthophylls such as lutein and zeaxanthin, and carotenes, such as beta-carotene, alpha-carotene, zeto-carotene, and lycopene and related molecules, including 1-HO-3',4'-didehydrolycopene, 3, 1'-(HO)2-gamma-carotene, 1,1'-(HO)2-3, 4, 3',4'-tetradehydrolycopene, 1, 1'-(HO)2-3, 4-didehydrolycopene.

Other suitable carotenoid compounds which may be used as described herein include hydrocarbons, such as lycopersene (7,8,11,12,15,7',8',11',12',15'-decahydro-γ,γ-carotene), phytofluene, hexahydrolycopene (15-cis-7,8,11,12,7',8'-hexahydro-γ,γ-carotene), torulene (3',4'-didehydro-β,γ-carotene) and α-zeacarotene (7',8'-dihydro-ε,γ-carotene); alcohols, such as alloxanthin, cynthiaxanthin, pectenoxanthin, cryptomonaxanthin, ((3r,3'r)-7,8,7',8'-tetradehydro-β,β-carotene-3,3'-diol), crustaxanthin (β,-carotene-3,4,3',4'-tetrol), gazaniaxanthin ((3r)-5'-cis-β,γ-caroten-3-ol), oh-chlorobactene (1',2'-dihydro-f,γ-caroten-1'-ol), loroxanthin (β,ε-carotene-3,19,3'-triol), lycoxanthin (γ,γ-caroten-16-ol), rhodopin (1,2-dihydro-γ,γ-caroten-1-ol), rhodopinol (aka warmingol; 13-cis-1,2-dihydro-γ,γ-carotene-1,20-diol), saproxanthin (3',4'-didehydro-1',2'-dihydro-β,γ-carotene-3,1'-diol) and zeaxanthin; glycosides, such as oscillaxanthin (2,2'-bis(β-l-rhamnopyranosyloxy)-3,4,3',4'-tetradehydro-1,2, 1',2'-tetrahydro-γ,γ-carotene-1,1'-diol), and phleixanthophyll (1'-(β-d-glucopyranosyloxy)-3',4'-didehydro-1',2'-dihydro-β,γ-caroten-2'-ol); ethers, such as rhodovibrin (1'-methoxy-3',4'-didehydro-1,2,1',2'-tetrahydro-γ,γ-caroten-1-ol) and spheroidene (1-methoxy-3,4-didehydro-1,2,7',8'-tetrahydro-γ,γ-carotene), epoxides, such as diadinoxanthin (5,6-epoxy-7',8'-didehydro-5, 6-dihydro-carotene-3,3-diol), luteoxanthin (5,6: 5',8'-diepoxy-5,6,5',8'-tetrahydro-β,β-carotene-3,3'-diol), mutatoxanthin, citroxanthin, zeaxanthin (furanoxide 5,8-epoxy-5,8-dihydro-β,β-carotene-3,3'-diol), neochrome (5',8'-epoxy-6,7-didehydro-5,6,5',8'-tetrahydro-β,β-carotene-3,5,3'-triol), foliachrome, trollichrome, and vaucheriaxanthin (5',6'-epoxy-6,7-didehydro-5,6,5',6'-tetrahydro-β,β-carotene-3,5,19,3'-tetrol); aldehydes, such as rhodopinal, wamingone (13-cis-1-hydroxy-1,2-dihydro-γ,γ-caroten-20-al), torularhodinaldehyde (3',4'-didehydro-β,γ-caroten-16'-al); acids and acid esters, such as torularhodin (3',4'-didehydro-β,γ-caroten-16'-oic acid) and torularhodin methyl ester (methyl 3',4'-didehydro-β,γ-caroten-16'-oate); ketones, such as astaxanthin, canthaxanthin (aka aphanicin), chlorellaxanthin (β,β-carotene-4,4'-dione), capsanthin ((3r, 3's,5'r)-3,3'-dihydroxy-β,κ-caroten-6'-one), capsorubin ((3s, 5r,3's,5'r)-3,3'-dihydroxy-κ,κ-carotene-6,6'-dione), cryptocapsin ((3'r,5'r)-3'-hydroxy-β,κ-caroten-6'-one), 2,2'-diketospirilloxanthin (1,1'-dimethoxy-3,4,3',4'-tetradehydro-1,2,1',2'-tetrahydro-γ,γ-carotene-2,2'-dione), flexixanthin (3,1'-dihydroxy-3',4'-didehydro-1',2'-dihydro-β,γ-caroten-4-one), 3-oh-canthaxanthin (aka adonirubin; aka phoenicoxanthin; 3-hydroxy-β,β-carotene-4,4'-dione), hydroxyspheriodenone (1'-hydroxy-1-methoxy-3, 4-didehydro-1,2,1',2',7',8'-hexahydro-γ,γ-caroten-2-one), okenone (1'-methoxy-1',2'-dihydro-c,γ-caroten-4'-one), pectenolone (3,3'-dihydroxy-7',8'-didehydro-β,β-caroten-4-one), phoeniconone (aka dehydroadonirubin; 3-hydroxy-2,3-didehydro-β,β-carotene-4,4'-dione), phoenicopterone (β,ϵ-caroten-4-one), rubixanthone (3-hydroxy-β,γ-caroten-4'-one), siphonaxanthin (3,19,3'-trihydroxy-7,8-dihydro-β,ϵ-caroten-8-one); esters of alcohols, such as astacein (3,3'-bispalmitoyloxy-2,3,2',3'-tetradehydro-β,β-carotene-4,4'-dione or 3,3'-dihydroxy-2,3,2',3'-tetradehydro-β,β-carotene-4,4'-dione dipalmitate), fucoxanthin (3'-acetoxy-5,6-epoxy-3,5'-dihydroxy-6',7'-didehydro-5,6,7,8,5',6'-hexahydro-β,β-caroten-8-one), isofucoxanthin (3'-acetoxy-3,5,5'-trihydroxy-6',7'-didehydro-5,8,5',6'-tetrahydro-β,β-caroten-8-one), physalien, zeaxanthin dipalmitate ((3r,3'r)-3,3'-bispalmitoyloxy-β,β-carotene or (3r,3'r)-β,β-carotene-3,3'-diol dipalmitate) and siphonein (3,3'-dihydroxy-19-lauroyloxy-7,8-dihydro-β,ϵ-caroten-8-one or 3,19,3'-trihydroxy-7,8-dihydro-β,ϵ-caroten-8-one 19-laurate); apo carotenoids, such as β-apo-2'-carotenal (3',4'-didehydro-2'-apo-b-caroten-2'-al), apo-2-lycopenal, apo-6'-lycopenal (6'-apo-y-caroten-6'-al), azafrinaldehyde (5,6-dihydroxy-5,6-dihydro-10'-apo-β-caroten-10'-al), bixin (6'-methyl hydrogen 9'-cis-6,6'-diapocarotene-6,6'-dioate), citranaxanthin (5',6'-dihydro-5'-apo-β-caroten-6'-one or 5',6'-dihydro-5'-apo-18'-nor-β-caroten-6'-one or 6'-methyl-6'-apo-β-caroten-6'-one), crocetin (8,8'-diapo-8,8'-carotenedioic acid), crocetinsemialdehyde (8'-oxo-8,8'-diapo-8-carotenoic acid), crocin (digentiobiosyl 8,8'-diapo-8,8'-carotenedioate), hopkinsiaxanthin (3-hydroxy-7,8-didehydro-7',8'-dihydro-7'-apo-b-carotene-4,8'-dione or 3-hydroxy-8'-methyl-7,8-didehydro-8'-apo-b-carotene-4,8'-dione), methyl apo-6'-lycopenoate (methyl 6'-apo-y-caroten-6'-oate), paracentrone (3,5-dihydroxy-6,7-didehydro-5,6,7',8'-tetrahydro-7'-apo-b-caroten-8'-one or 3,5-dihydroxy-8'-methyl-6,7-didehydro-5, 6-dihydro-8'-apo-b-caroten-8'-one) and sintaxanthin (7',8'-dihydro-7'-apo-b-caroten-8'-one or 8'-methyl-8'-apo-b-caroten-8'-one); nor and seco carotenoids, such as actinioerythrin (3,3'-bisacyloxy-2,2'-dinor-b,b-carotene-4, 4'-dione), β-carotenone (5,6:5',6'-diseco-b,b-carotene-5,6,5', 6'-tetrone), peridinin (3'-acetoxy-5,6-epoxy-3,5'-dihydroxy-6',7'-didehydro-5,6,5',6'-tetrahydro-12',13',20'-trinor-b,b-caroten-19,11-olide), pyrrhoxanthininol (5,6-epoxy-3,3'-dihydroxy-7',8'-didehydro-5,6-dihydro-12',13',20'-trinor-b, b-caroten-19,11-olide), semi-α-carotenone (5,6-seco-b,e-carotene-5,6-dione), semi-β-carotenone (5,6-seco-b,b-carotene-5,6-dione or 5',6'-seco-b,b-carotene-5',6'-dione) and triphasiaxanthin (3-hydroxysemi-b-carotenone 3'-hydroxy-5,6-seco-b,b-carotene-5,6-dione or 3-hydroxy-5',6'-seco-b,b-carotene-5',6'-dione); retro carotenoids and retro apo carotenoids, such as eschscholtzxanthin (4',5'-didehydro-4,5'-retro-b,b-carotene-3,3'-diol), eschscholtzxanthone (3'-hydroxy-4',5'-didehydro-4,5'-retro-b,b-caroten-3-one), rhodoxanthin (4',5'-didehydro-4,5'-retro-b,b-carotene-3,3'-dione) and tangeraxanthin (3-hydroxy-5'-methyl-4,5'-retro-5'-apo-b-caroten-5'-one or 3-hydroxy-4,5'-retro-5'-apo-b-caroten-5'-one); and higher carotenoids, such as nonaprenoxanthin (2-(4-hydroxy-3-methyl-2-butenyl)-7',8', 11',12'-tetrahydro-e,y-carotene), decaprenoxanthin (2,2'-bis (4-hydroxy-3-methyl-2-butenyl)-e,e-carotene), c.p. 450 (2-[4-hydroxy-3-(hydroxymethyl)-2-butenyl]-2'-(3-methyl-2-butenyl)-b,b-carotene), c.p. 473 (2'-(4-hydroxy-3-methyl-2-butenyl)-2-(3-methyl-2-butenyl)-3',4'-didehydro-1',2'-dihydro-b,y-caroten-1'-ol) and bacterioruberin (2,2'-bis(3-hydroxy-3-methylbutyl)-3,4,3',4'-tetradehydro-1,2,1',2'-tetrahydro-y,y-carotene-1,1'-dio)

A carotenoid particle as described herein may contain a single carotenoid compound (e.g. lycopene) or more than one carotenoid compound (e.g. lycopene and beta-carotene). Typically, each carotenoid compound will be present in a range of different isomeric forms.

In some preferred embodiments, the carotenoid compound is lycopene. Lycopene is an open-chain unsaturated $C_{40}$ carotenoid of structure I (Chemical Abstracts Service Registry Number 502-65-8).

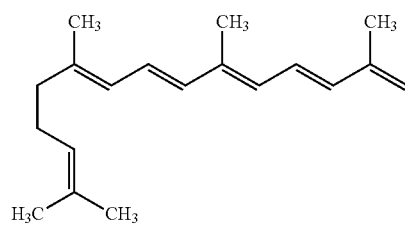
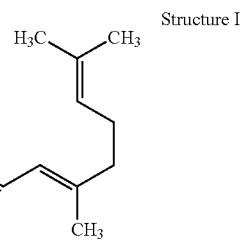

Structure I

Lycopene occurs naturally in plants such as tomatoes, guava, rosehip, watermelon and pink grapefruit.

Lycopene for use as described herein may comprise one or more different isomers. For example, lycopene may comprise at least 10%, at least 20%, at least 30%, at least 40%, at least 50%, at least 60%, at least 70%, at least 80%, at least 90%, or at least 95% (Z)-isomers, (all-E)-isomers, or cis-isomers, such as 5-cis- or 9-cis- or 13-cis-isomers, which have improved bioavailability relative to trans isomers. Trans isomers may isomerise into cis forms in vivo, or during storage and processing. Carotenoid particles comprising lycopene may be referred to herein as Lycosomes™.

Carotenoid compounds for use as described herein may be natural i.e. obtained from a natural source, for example, extracted from a plant, such as a tomato or melon. A range of methods for extracting, concentrating and/or purifying carotenoids from plants are known in the art. For example, solvent extraction using ethanol, DMSO, ethyl acetate, hexane, acetone, soya or other vegetable oil, or non-vegetable oils may be employed. A carotenoid compound may be isolated i.e. free or substantially free of other molecules found in its natural source or environment.

Carotenoid compounds for use as described herein may be synthetic i.e. produced by artificial means, for example, by chemical synthesis or fermentation. A range of methods for chemical synthesis of lycopene and other carotenoids are known in the art. For example, a three-stage chemical synthesis based on the standard Wittig olefination reaction scheme for carotenoid synthesis may be employed, in which an organic solution of $C_{15}$ phosphonium methanesulfonate in dichloromethane (DCM) and an organic solution of $C_{10}$ dialdehyde in toluene are produced, and the two organic solutions are gradually combined with sodium methoxide solution and undergo a condensation reaction to form crude lycopene. The crude lycopene may then be purified using routine techniques, for example by adding glacial acetic acid and deionized water to the mixture, stirring vigorously, allowing the aqueous and organic phases to separate, and extracting the organic phase containing DCM and crude lycopene with water. Methanol is added to the organic phase and the DCM removed via distillation under reduced pressure. The crude methanolic lycopene solution is then be heated and cooled to crystalline slurry that is filtered and washed with methanol. The lycopene crystals may then be recrystallized and dried under heated nitrogen. Synthetic carotenoids, such as lycopene, are also available from commercial suppliers (e.g. BASF Corp, NJ USA, DSM Nutritional Products, Basel, CH).

Synthetic carotenoids may comprise an increased proportion of cis isomers relative to natural carotenoids. For example, synthetic forms of carotenoids such as lycopene may be up to 25% 5-cis, 1% 9-cis, 1% 13-cis, and 3% other cis isomers, whilst natural forms of carotenoids, for example lycopene produced by tomatoes, may be 3-5% 5-cis, 0-1% 9-cis, 1% 13-cis, and <1% other cis isomers. Since cis-carotenoids, such as cis-lycopene, have increased bioavailability relative to trans-carotenoids, such as trans-lycopene, synthetic carotenoids may be preferred in some embodiments.

Derivatives of carotenoids as described above may be produced by chemical synthesis analogous to the synthesis described above; by chemical modification of natural carotenoids extracted from plant material or by microbial, yeast, algal, or fungal fermentation. For example, lycopene may be produced by fermentation of the fungus *Blakeslea trispora* (e.g. Lyconat™, Vitatene SA).

The population of carotenoid particles may comprise 0.05 to 90% by weight of the carotenoid compound, preferably 0.1% to 10% by weight. For example, the population may be 0.01% or more, 0.05% or more, 0.1% or more, 0.2% or more, 0.5% or more, 1% or more, 10% or more, or 20% or more by weight of carotenoid compound. The population may be up to 90%, up to 80%, up to 70%, up to 60% up to 50%, up to 40%, up to 30%, up to 20% or up to 10% by weight of carotenoid compound.

The carotenoid particles in the population may contain the same or similar amounts of carotenoid compound or the amount of carotenoid compound may vary between particles in the population. Each carotenoid particle in the population may comprise 0.05 to 90% by weight of carotenoid compound. For example, each carotenoid particle in the population may be 0.05% or more, 0.1% or more, 1% or more, 10% or more, or 20% or more by weight of carotenoid molecules. Each carotenoid particle may be up to 90%, up to 80%, up to 70%, up to 60% up to 50%, up to 40% or up to 30%, up to 90% or more by weight of carotenoid compound.

The extent of particle variability within a population may vary depending on the production method. Preferably, at least 80%, at least 90%, at least 95%, at least 98% or at least 99%, for example 85% to 95%, of the carotenoid particles in the population contain the same or similar amounts of carotenoid compound.

Typically, a population of carotenoid particles may be comprised in a unit dosage formulation which contains 1 to 10 mg of carotenoid compound, such as lycopene, for example about 3.5 mg lycopene.

The cargo molecule which is incorporated into the carotenoid particle may be any compound, agent, drug or other product or combination thereof, which needs to be delivered to the blood stream. Typically, the cargo molecule will be a therapeutic or nutritional compound, such as a pharmaceutical, nutraceutical or a dietary or nutritional supplement.

Cargo molecules which are labile in the gastro-intestinal tract or poorly absorbed by the gastro-intestinal tract are especially suitable for incorporation into carotenoid particles.

Suitable cargo molecules include products of the fermentation, oxidation, processing or degradation of foods such as meat, fish, dairy, grain, bean, honey, tea or other foodstuffs or beverages. Products may include whey protein or peptides, carbohydrates, such as poly- or oligosaccharides, lipids, flavones, and other food derived bioactive molecules. Bioactive molecules may, for example, include antimicrobial peptides, defensins, cathelidins, whey acid proteins, bioactive fragments of food proteins; and peptides which display one or more of protease inhibiting, bactericidic, metabolic, anti-inflammatory, immune-stimulating, coagulation, angiogenesis and proliferation control activities, or exert a beneficial effect on neurotransmitters, angiotensin, hormones and/or other signalling pathways.

Suitable cargo molecules also include products of probiotic bacteria, yeast or other microbial metabolism, or the metabolism of fungi or moulds, in particular organisms which are used in food and beverage manufacturing or are associated therewith. Examples include bacteria such as Lactobacilli spp for example *L. acidophilus, L. casei, L. lactis, L. plantarum, L. reuteri, L. rhamnosus, L. actococcus, L. garvieae* and *L. bulgaricus*; Lactococci, such as *L. raffinolactis*; Bifidobacteria, such as *B. animalis, B. breve* and *B. longu; E. coli* such as *E. coli* M-17, *E. coli* Nissle 1917; Enterococci, such as *Enterococcus faecium* MG004 and Streptococci, such as *Streptococcus thermophilus*; yeasts, such as *Dekkera intermedia*, Candida, such as *C. blankii* and *C. stellatam*; Saccharomyces, such as *S. cerevisiae, S. pastorianus, S. exiguus, S. boulardii* and *S. varum*; Brettanomyces, such as *B. bruxellensis* and *B. lambicus; Schizosaccharomyces pombe, Torulaspora delbrueckii* and *Zygosaccharomyces bailii*; moulds, for example *Aspergillus* spp, such as *A. oryzaeor, A. soyae, A. sojae, A. niger, A. terreus, A. tamari* and *A. flavus; Monascus* spp, such as *M. pupureus, M. ruber*, and *M. pilosus; Penicillium* spp, such as *P. chrysogenum, P. roqueforti, P. glaucum, P. candidum, P. camemberti, P. paneum, P. geotrichum, P. solitum, P. nalgiovense, P. commune, P. olsonii, P. verrucosum, P. oxalicum*, and *P. viridicatum; Tolypocladium inflatum; Rhizopus* spp, such as *R. artocarpi, R. nigricans, R. oligosporus, R. oryzae* and *R. stolonifer; Neurospora* spp such as *N. sitophilia* and *N. intermedia*; and *Fusarium venenatum*.

Other suitable cargo molecules include lecithin, carbohydrates; amino acids; flavones, such as luteolin, apigenin, and tangeritin; flavonols, such as quercetin, rutin, kaempferol, myricetin, fisetin, isorhamnetin, pachypodol and rhamnazin; flavanones, such as hesperetin, naringenin, eriodictyol and homoeriodictyol; flavanonols, such as taxifolin (or dihydroquercetin), and dihydrokaempferol; isoflavones, such as genistein, daidzein and glycitein; catechins, gallocatechin, catechin 3-gallate, gallocatechin 3-gallate, epicatechins, epigallocatechin, epicatechin 3-gallate, flavon-3-ols such as epigallocatechin 3-gallate; proanthocyanidins, for example as dimers, trimers, oligomers, or polymers with flavanols; anthocyanidins, such as cyanidin, delphinidin, malvidin, pelargonidin, peonidin, and petunidin, aglycones of anthocyanins, such as betalain, amaranthine and isoamaranthine; silibinin or silymarin, curcuminoids, gingerols, ceramides; isoprene, prenol, isovaleric acid, geranyl pyrophosphate, eucalyptol, limonene, pinene, farnesyl pyrophosphate, artemisinin, bisabolol, geranylgeranyl pyrophosphate, retinol, retinal, phytol, taxol, forskolin, aphidicolin, squalene, lanosterol, and other terpenes and terpenoids; sterols and sterol esters, such as stanol ester; phytosterols; alpha-, beta-, gamma- and delta-tocotrienols; shark or other cartilaginous fish oils, vegetable oils, or oils from amaranth seed, rice, wheat germ or olives; squalenes; retinoids; garlic acid or salicylic acid or other hydrolysable tannins; cinnamic acid; lignins; polyphenols, such as catechol, hydroquinone, 2,6-dimethoxybenzoquinone, 3-acetyl-6-methoxybenzaldehyde, tyrosol, p-hydroxyphenylacetic acid, caffeic, ferulic acids, myristicin, eugenol, umbelliferone, aesculetin, bergenon, eugenin, juglone, plumbagin, mangiferin, resveratrol(3,5,4'-trihydroxy-trans-stilbene), emodin, cyanidin, pinoresinol, eusiderin, amentoflavone, ellagic acid, theaflavin, thearubigins, catechol melanins, condensed tannins, phlorotannins, and other polyphenols; vitamins, such as niacin (vitamin B3), folic acid (vitamin B9), ascorbic acid (vitamin C), riboflavin (vitamin B2), thiamine (vitamin B1), calciferol (vitamin D), cobalamins (vitamin 12), phylloquinone (vitamin K1), pantothenic acid (vitamin B5), biotin (vitamin B7) and pyridoxine (vitamin B6), minerals, such as calcium, selenium, chromium, magnesium, iron, zinc, copper and other metal ions; penicillins, cephalosporins, cardapenems, sulphonamides, quinolones, oxazodinones, macrolides and other antibiotics, anti-viral, anti-fungi, and anti-parasite drugs, in particular drugs targeting liver and other organs which express carotenoid receptors, such as liver, adrenal glands, lymphocytes, lymph nodes, prostate tissues, and testis; and statins, such as atorvastatin, cerivastatin, fluvastatin, lovastatin, mevastatin, pitavastatin, pravastatin, rosuvastatin, and simvastatin, either alone or in complexes or combinations.

A particle may contain a single type of cargo molecule or more than one type of cargo molecule, for example two, three, four or more different types of cargo molecule.

The carotenoid particle may comprise 0.05 to 90% by weight of cargo molecules. For example, the carotenoid particle may be 0.1% or more, 1% or more, 10% or more, or 20% or more by weight of cargo molecules. The carotenoid particle may be up to 90%, up to 80%, up to 70%, up to 60% up to 50%, up to 40% or up to 30%, up to 90% or more by weight of cargo molecules.

The ratio of carotenoid compound to cargo molecule in the carotenoid particle by weight may be 0.001 or more, 0.01 or more, 0.1 or more, 0.2 or more or 0.5 or more. The ratio of carotenoid compound to cargo molecule in the carotenoid particle by weight may be up to 1000, up to 100, up to 10, up to 5, or up to 2.

In some embodiments, a carotenoid particle may comprise lycopene and whey protein in the ratio (w/w) of 0.05 to 1. preferably 0.1. For example, a population of carotenoid particles in a unit dosage format may contain 2 to 5 mg, for example 3.5 mg, of lycopene and 20 to 50 mg, for example 35 mg, of whey protein.

In other embodiments, a carotenoid particle may comprise lycopene and resveratrol in a ratio (w/w) of from 0.02 to 0.2, preferably from 0.06 to 0.08. For example, a population of carotenoid particles in a unit dosage format may contain 2 to 5 mg, for example 3.5 mg, of lycopene and 30 to 70 mg, for example 50 mg, of resveratrol.

In other embodiments, a carotenoid particle may comprise lycopene and a statin, such as simvastatin, in a ratio (w/w) of from 0.1 to 0.5, preferably 0.3 to 0.4, for example 0.35. For example, a population of carotenoid particles in a unit dosage format may contain 2 to 10 mg, for example 7 mg, of lycopene and 20 mg of statin.

The bioavailability of the cargo molecule in circulation following oral administration of carotenoid particles incorporating the cargo molecule may be increased relative to bioavailability following oral administration of the cargo molecule alone.

Increased bioavailability may allow the dosage of the cargo molecule to be reduced when it is incorporated into carotenoid particles as described herein compared to administration without the particles, whilst achieving the same efficacy. This may be useful in reducing side-effects associated with the cargo molecule. For example, the dosage of the cargo molecule incorporated into a carotenoid particle may be 1% or less, 5% or less, 10% or less, 20% or less, 30% or less, 40% or less or 50% or less of the dosage of the cargo molecule on its own which is required for the same efficacy.

The bioavailability of the cargo molecule may be increased by two fold or more, three fold or more or four fold or more by incorporation into carotenoid particles as described herein. For example, the data herein shows that the bioavailability of resveratrol is increased by two fold and the bioavailability of simvastatin is increased by four fold by incorporation into a carotenoid particle. In some embodiments, the cargo molecule may display no bioavailability or substantially no bioavailability when it is administered without incorporation into a carotenoid particle. For example, whey protein is shown to display little or no bioavailability when administered orally without incorporation into a carotenoid particle.

At the same dosage, the efficacy of the cargo molecule may be increased when it is incorporated into carotenoid particles as described herein compared to its efficacy without such incorporation. For example, the efficacy of the cargo molecule incorporated into a carotenoid particle may be increased by 2 fold or more, 3 fold or more, 5 fold or more, 10 fold or more or 100 fold or more compared to the efficacy of the same dosage of cargo molecule on its own.

Carotenoid particles as described herein may be useful in targeting cargo molecules to tissues which express carotenoid receptors.

A method of improving the delivery of a cargo molecule to a target tissue which expresses carotenoid receptors may comprise:
  incorporating the cargo molecule into a carotenoid particle as described herein and,
  administering the carotenoid particle to an individual.

Tissues which express carotenoid receptors include hepatocytes, liver, adrenal glands, lymphocytes, lymph nodes, prostate tissues and testis. In some preferred embodiments, the target tissue which expresses carotenoid receptors is liver.

Suitable cargo molecules may include compounds which are beneficially targeted to tissues which express carotenoid receptors, such as the liver.

Suitable cargo molecules for delivery to the liver include prodrugs which are activated in the liver, for example by the action of liver enzymes. Prodrugs which are activated by liver enzymes include aldehyde oxidase activated prodrugs, such as 5-ethynalyl-2(1H)-pyrimidinone, 5-iodo-2-pyrimidinone-2'-deoxyribose (IPdR), and 5-fluoro-2-pyrimidinone (5-FP); cytochrome P450 reductase activated prodrugs, such as menadione, mitomycin C, tirapazamine and EO9 (3-hydroxymethyl-5-aziridinyl-1-methyl-2[1H-indole4,7-dione] prop-2-en-1-ol); cytochrome p450 activated prodrugs, such as 4-ipomeanol, ftorafir, dacarbazine, trofosamide, ifosamide, cyclophosphamide, and 1,4-bis-{[2-(dimethylamino-N-oxide)ethyl]amino}-5,8-dihydroxyanthracene-9,10-dione (AQ4N); thymidine phosphorylase activated prodrugs such as 5'-deoxy-5-fluorouridine, and glutathione transferase activated prodrugs, such as γ-Glutamyl-α-amino-β(2-ethyl-N,N,N',N'-tetrakis(2-chloroethyl)phosphoro-diamidate)sulfonyl-propionyl)-(R)-(–)phenylglycine (Ter286), S-CPHC-ethylsulfoxide (S-(N-p-chlorophenyl-N-hydroxycarbamoyl) ethylsulfoxide) and cis-3-(9H-Purin-6-ylthio)acrylic acid (PTA).

Other suitable prodrugs are well-known in the art and include lisdexamphetamine, codeine and tramadol.

Administration of carotenoid particles incorporating the cargo molecule may increase the concentration of the cargo molecule in the target tissue following relative to the concentration after administration of the same dose of cargo molecule on its own.

Administration of the carotenoid particle incorporating the cargo molecule may provide a decreased concentration of the cargo molecule in non-target tissue following relative to the concentration after administration of the same dose of cargo molecule on its own Methods as described herein are generally useful in increasing the availability of cargo molecules. A method of increasing the bioavailability of a cargo molecule may comprise:

incorporating the cargo molecule into a carotenoid particle as described herein.

Following incorporation of the cargo molecule into the carotenoid particles, and optional formulation into a composition, such as a pharmaceutical composition, food additive or dietary supplement, the carotenoid particles may be administered to an individual.

In some embodiments, the cargo molecule may be whey protein. Whey protein is shown herein to possess anti-*Chlamydia* and cholesterol lowering activity. Whey protein is a collection of globular proteins which are naturally found in milk. It is isolated from whey, which is a by-product of cheese manufacture. It is a mixture of beta-lactoglobulin (~65%), alpha-lactalbumin (~25%), and serum albumin (~8%), which are soluble in their native forms, independent of pH. Whey protein is commercially available from a number of suppliers (e.g. Euросérum, France).

In some embodiments, the cargo molecule is not a lactoprotein, such as casein, beta-lactoglobulin, alpha-lactalbumin, and serum albumin. In such embodiments, carotenoid particles as described herein may be devoid of lactoproteins.

In some embodiments, the cargo molecules are not whey proteins and/or whey peptides. In such embodiments, carotenoid particles as described herein may be devoid of whey proteins and/or whey peptides.

In some preferred embodiments, the carotenoid particle may further comprise lecithin. Lecithin (E222) is commonly used as an emulsifier in food products and may be isolated from egg yolk or animal or soy or other plant tissue. Lecithin comprises a number of fatty acids, phospholipids, triglycerides, and glycolipids, as well as glycerol, choline and phosphoric acid. Lecithin is widely available commercially. Lecithin may include soy-lecithin.

A carotenoid particle as described herein may comprise from 1.5% to 98.5% (w/w) lecithin. For example, a particle may comprise at least 1.5%, at least 5%, or at least 10% (w/w) lecithin. A particle may comprise up to 98.5%, up to 90%, or up to 80% (w/w) lecithin.

The ratio of lecithin to carotenoid molecule in the carotenoid particle by weight may be 0.1 or more, 1 or more, 10 or more, or 20 or more. The ratio of lecithin to carotenoid molecule in the carotenoid particle by weight may be up to 1000, up to 500, up to 200, or up to 100.

The ratio of lecithin to cargo molecule in the carotenoid particle by weight may be 0.01 or more, 0.1 or more, 1 or more, or 2 or more. The ratio of lecithin to cargo molecule in the carotenoid particle by weight may be up to 100, up to 50, up to 20, or up to 10.

In some embodiments, a carotenoid particle may comprise lycopene, whey protein and lecithin in the ratio (w/w) of about 1:10:50. For example, a population of carotenoid particles in a unit dosage format may contain 3.5 mg of lycopene, 35 mg of whey protein and 175 mg lecithin.

Carotenoid particles as described herein may be packaged into chylomicrons upon absorption from the gastrointestinal tract for transport through the blood stream. The size of the particles is preferably suitable for chylomicron packaging. Carotenoid particles may be fine (100 nm to 2.5 μm), or ultrafine (1 to 100 nm). For example, the carotenoid particles may be from 0.1 nm to 1 μm in size, preferably 1 to 900 nm. more preferably 10 to 800 nm.

A suitable particle may be from 0.1 nm to 1 μm in its longest dimension (e.g. length, width, height and/or diameter). Preferably, all of the dimensions of the particle are from 0.1 nm to 1 m.

Particle size may be determined by any convenient technique. For example, sieve analysis, laser diffraction, or photoanalysis.

A population of carotenoid particles may be uniform size (i.e. have a low size distribution) or non-uniform (i.e. have a high size distribution).

Preferably, at least 85%, at least 90%, at least 95% or at least 99% of the particles in the population display uniform size or substantially uniform size (e.g. within 5% or within 10% of the mean particle size).

A population of carotenoid particles may contain particles having a range of different shapes and sizes.

In some embodiments, a population of carotenoid particles may comprise inverse micelles in which carotenoids molecules are encapsulated by an outer later of cargo molecules, the hydrophobic structures of the cargo molecules facing the interior.

In some embodiments, a population of carotenoid particles may comprise aggregates comprising a carotenoid matrix which is embedded with hydrophobic parts of the cargo molecules. A range of different amphiphilic particles may be produced, depending on the nature and amount of the embedded and exposed regions of the cargo molecules.

When parts of the cargo molecule remain on the exterior of the carotenoid particle, the particles in the population may form clusters or aggregates. The size and shape of these clusters depends on the architecture of the cargo molecules and may also be influenced by the presence of other molecules, which may interact or complex with the cargo molecules.

Carotenoid particles as described herein may be produced by any convenient method.

In some embodiments, a population of carotenoid particles may be produced by a method comprising:
dissolving a carotenoid compound in a first solvent to produce a first solution and a cargo molecule in a second solvent to produce a second solution, and
admixing the first and second solutions under conditions which allow the cargo molecule to incorporate into the matrix of the carotenoid compound.

The carotenoid compound may be dissolved in any suitable pharmaceutically compatible solvent, for example oil, acetone, ethanol or isopropanol, most preferably ethanol or vegetable oil.

The cargo molecule may be dissolved in any suitable pharmaceutically compatible solvent. Suitable solvents include water, oil, acetone, ethanol or isopropanol. The choice of solvent will depend on the cargo molecule. For example, whey protein may be dissolved in water and resvertrol and statins, such as simvastatin, may be dissolved in ethanol. The skilled person is readily able to identify a suitable solvent for any given cargo molecule using readily available information or standard analytical techniques.

The first solvent and the second solvent may be the same or different depending on the carotenoid and cargo molecule used.

The carotenoid and the cargo molecule may be completely soluble in the first and second solvents or sufficiently soluble to facilitate incorporation of the cargo molecule, or its hydrophobic moieties, into the carotenoid matrix.

The first and second solutions may be mixed under conditions which allow the formation of matrix of carotenoid compound which incorporates the cargo molecule. For example, when an aqueous solution of cargo molecules is mixed with a solution of carotenoid compound in ethanol, a solvent/water ratio by volume of the order of 60/40 may be chosen.

Without being bound by any theory, carotenoid particles are driven to form spontaneously in solution through thermodynamics and the balance between entropy and enthalpy.

In aqueous solution, the hydrophobicity of the carotenoid compound drives the formation of particles, even though assembling molecules together into particles leads to a reduction in entropy. At very low concentrations of carotenoid, only monomers are present in true solution. As the concentration of the carotenoid increases, a point is reached at which unfavourable entropy considerations derived from the hydrophobic hydrocarbon chain of the carotenoid become dominant. At this point, the hydrophobic end of the carotenoid is sequestered away from the water and carotenoid particles start to form. Above the critical carotenoid concentration, the entropic penalty of assembling the carotenoid monomers into particles is less than the entropic penalty of caging the carotenoid monomers with water molecules.

After mixing, the mixture of the first and second solvents may be left to stand for 30 to 60 min at a temperature slightly higher than ambient temperature. The solvents may then be evaporated or the mixture spray dried to produce a composition in emulsion or dispersion form. Evaporation may be conveniently achieved using reduced pressure (e.g. 200 to 300 mbar). The composition may then be further treated, for example by drying to produce a powder or by heat-treating to produce a gel.

In other embodiments, carotenoid particles as described herein may be produced by a method comprising:
dissolving a carotenoid compound in a first solvent to produce a first solution,
admixing the first solution with dried particles of the cargo molecule under conditions which allow the dried particles to be incorporated in liquid carotenoid droplets.

For example, lycopene dissolved in ethanol or acetone solution may be sprayed over a powder of dry particles of cargo molecule. When liquid droplets of lycopene crystallise on the surface of the powder, some of the dry particles are mechanically captured by the lycopene crystals.

The first solvent may then be dried out or evaporated to produce carotenoid particles in concentrated and/or dried form which incorporate the cargo molecule. Alternatively, the mixture of the pre-solubilised lycopene and the initially dried product may remain in a form of a suspension or emulsion in the first solvent.

In some embodiments, carotenoid particles may be produced by sonication of the mixture of first and second solutions. Sonication may be especially useful in admixing carotenoid compounds and cargo molecules which are dissolved in immiscible solvents. Ultrasound energy allows molecules to transiently cross the thermodynamic barrier imposed by the solvent environments, allowing blending and the formation of carotenoid particles, such as lycosome micelles.

In some embodiments, carotenoid particles may be produced by spray-drying the mixture of first and second solutions.

In some embodiments, lecithin may be incorporated into the carotenoid particles. In some embodiments, lecithin may be admixed with the first and second solutions. Alternatively, lecithin dissolved in oil may be admixed with the concentrated or dried admixture comprising the carotenoid particles after evaporation and/or spray drying.

While it is possible for carotenoid particles to be administered alone, it is preferable to present them as a composition (e.g., formulation), such as a food product, food additive, fortified food, dietary supplement, nutraceutical or pharmaceutical composition which comprises carotenoid particles, as defined above, together with one or more pharmaceutically or nutritionally acceptable carriers, adjuvants, excipients, diluents, fillers, buffers, stabilisers, flavourings, preservatives, sweeteners, colourings, lubricants, or other materials well known to those skilled in the art and optionally other food products, dietary supplements or nutraceutical, therapeutic or prophylactic agents.

Compositions or formulations comprising carotenoid particles as defined above, for example carotenoid particles admixed together with one or more pharmaceutically or nutraceutically acceptable carriers, excipients, buffers, adjuvants, stabilisers, or other materials, as described herein, may be used in the methods described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington's Pharmaceutical Sciences, 18th edition, Mack Publishing Company, Easton, Pa., 1990.

The term "nutraceutically acceptable" as used herein pertains to compounds, materials, compositions, and/or dosage forms which are in common or widespread usage in food and dietary products and are generally considered non-toxic, for example, compounds may have the US FDA designation "GRAS" (Generally Recognised as Safe), or equivalent food additive status in other jurisdictions.

The formulations may conveniently be presented in unit dosage form and may be prepared by any methods well known in the art of pharmacy, food science or nutrition. Such methods include the step of bringing the carotenoid particles into association with a carrier which may constitute one or more accessory ingredients. In general, the formulations are prepared by uniformly and intimately bringing into association the carotenoid particles with liquid carriers or finely divided solid carriers or both, and then if necessary shaping the product.

Formulations may be in the form of food products, beverages, liquids, solutions, suspensions, emulsions, elixirs, syrups, tablets, lozenges, granules, powders, capsules, cachets, pills, ampoules, ointments, gels, pastes, creams, sprays, mists, foams, lotions, oils, boluses, electuaries, or aerosols.

The carotenoid particles or compositions comprising the carotenoid particles are preferably in a form which is suitable for administration orally for delivery via the gastrointestinal tract. Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile.

Compositions for oral administration may further comprise sweeteners, texture modifiers, colourings and flavourings.

Aspects of the invention provide a method of producing a formulation, such as a nutraceutical or pharmaceutical composition, which has increased bioavailability of a cargo molecule comprising incorporating the cargo molecule into a carotenoid particle.

The cargo molecule may display increased bioavailability following oral administration when incorporated into a carotenoid particle relative to cargo molecule alone.

Methods of incorporating a cargo molecule into a carotenoid particle are described elsewhere herein.

Cargo molecules incorporated into carotenoid particles may be delivered via the blood stream to a tissue which expresses carotenoid receptors. Tissues which express carotenoid receptors may include hepatocytes, liver, adrenal glands, lymphocytes, lymph nodes, prostate tissues and testis. This may be useful in providing targeted delivery of an cargo molecule to a specific tissue.

An aspect of the invention provides the use of a carotenoid particle as described herein to deliver the cargo molecule to the blood stream via the gastrointestinal tract e.g. via oral administration.

Carotenoid particles as described herein may be used in methods of treatment of the human or animal body, including prophylactic treatment (e.g. treatment before the onset of a condition in an individual to reduce the risk of the condition occurring in the individual; delay its onset; or reduce its severity after onset). The method of treatment may comprise administering the carotenoid particles to an individual in need thereof.

Administration is normally in a "therapeutically effective amount" or "nutritionally effective amount", this being sufficient to show benefit to the individual. Such benefit may be at least amelioration of at least one symptom or physiological parameter.

Determining the optimal dosage for an individual will generally involve the balancing of the level of dietary or therapeutic benefit or efficacy associated with a particular dosage of cargo molecule against any risk or deleterious side effects associated with the dosage.

The selected dosage level will depend on a variety of factors including, but not limited to, the nature and activity of the cargo molecule, the purpose of the treatment, the time of administration, the rate of excretion of the cargo molecule, the duration of the treatment, other drugs, compounds, and/or materials used in combination, and the age, sex, weight, condition, general health, and prior medical history of the individual. The amount of carotenoid particles will ultimately be at the discretion of the physician, dietician or other healthcare or wellness professional.

Administration in vivo can be effected in one dose, continuously or intermittently (e.g., in divided doses at appropriate intervals) throughout the course of treatment. Single or multiple administrations can be carried out with the dose level and pattern being selected by the supervising professional.

In general, a suitable dose of the cargo molecule is in the range of about 0.01 mg to about 1000 mg per kilogram body weight of the subject per day.

For example, when cargo molecule is whey protein, the composition may be for administration at a dose of 0.1 mg/Kg/day to 1000 mg/Kg/day of whey protein. When cargo molecule is resveratrol, the composition may be for administration at a dose of 0.1 mg/Kg/day to 100 mg/Kg/day of resveratrol. When cargo molecule is a statin, the composition may be for administration at a dose of 0.01 mg/Kg/day to 2 mg/Kg/day of statin. When cargo molecule is isoflavone, the composition may be for administration at a dose of 0.1 mg/Kg/day to 10 mg/Kg/day of isoflavone.

Where the cargo molecule is a salt, an ester, prodrug, or the like, the amount administered is calculated on the basis of the parent compound and so the actual weight to be used is increased proportionately.

Individuals suitable for treatment as described herein include individuals with a condition which is completely or partially (e.g. at least one symptom of the condition) ameliorated or alleviated by the cargo molecule, individuals at an increased risk of suffering from such a condition or patients who are predisposed to or at increased risk of suffering from such a condition, relative to the general population.

The condition which is ameliorated or alleviated by the cargo molecule will depend on the nature of the cargo molecule.

For example, a carotenoid particle comprising whey protein as described herein may be useful in treating *Chlamydia* infection, liver infections and/or in lowering cholesterol, for example in individual with elevated cholesterol levels or hypercholesterolemia.

A carotenoid particle comprising a statin, may be useful in the treatment and/or prevention of cardiovascular disease, dementia, hypertension, cancer, including lung cancer, cataracts, and elevated cholesterol or hypercholesterolemia. Carotenoid particles comprising statins may also be useful in the treatment and/or prevention of other diseases and conditions which may be ameliorated by the pleotropic effects of statins, but for which statin treatment has not previously been use because of possible side effects, such as diabetes, in particular type II diabetes, and Alzheimer's disease.

Carotenoid particles comprising resveratrol may be useful in the treatment and/or prevention of metabolic syndrome or one or more symptoms thereof, such as elevated cholesterol and/or triglycerides, diabetes, cardio- and cerebro-vascular disease, cancer, acute and chronic bacterial, fungal and viral infections, Alzheimer's and other neurodegenerative diseases, gastointestinal tract diseases, connective tissue disease, arthritis, and inflammatory conditions, as well as in anti-aging and beauty products and increasing wellness and longevity.

Carotenoid particles comprising isoflavones may be useful in the treatment and prevention of metabolic syndrome or one or more symptoms thereof, such as elevated cholesterol and/or triglycerides, diabetes, cardio- and cerebro-vascular disease, cancer, Alzheimer's and other neurodegenerative diseases, connective tissue diseases, and inflammatory conditions, as well as in anti-aging and beauty products and increasing wellness and longevity.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures and tables described below.

BRIEF DESCRIPTION OF DRAWINGS

FIG. 1 shows the effect of whey protein on *C. trachomatis* in McCoy cells.

FIG. 3 shows comparative pharmacokinetics of two trans-Resveratrol products, free form and embedded into lycopene clusters.

FIGS. 4A to 4C show the effect on plasma cholesterol (FIG. 4A), plasma LDL (FIG. 4B), and plasma HDL (FIG. 4C) of simvastatin alone at 20 mg, 40 mg and 80 mg daily dose and simvastatin (20 mg) incorporated into a lycopene particle ("lycostatintin").

FIG. 6 shows the average serum concentrations of genistein in SI+lycopene patients (solid) and SI in lycopene particles patients (dashed).

FIG. 7 shows the average serum concentrations of daidzein in SI+lycopene patients (solid) and SI in lycopene particles patients (dashed).

FIG. 8 shows the average serum concentrations of lycopene in ng/ml in SI+lycopene patients (□) and SI in lycopene particles patients (◇).

FIG. 9 shows the serum concentrations of soy isoflavones in the serum of SI only patients.

Figure 2:
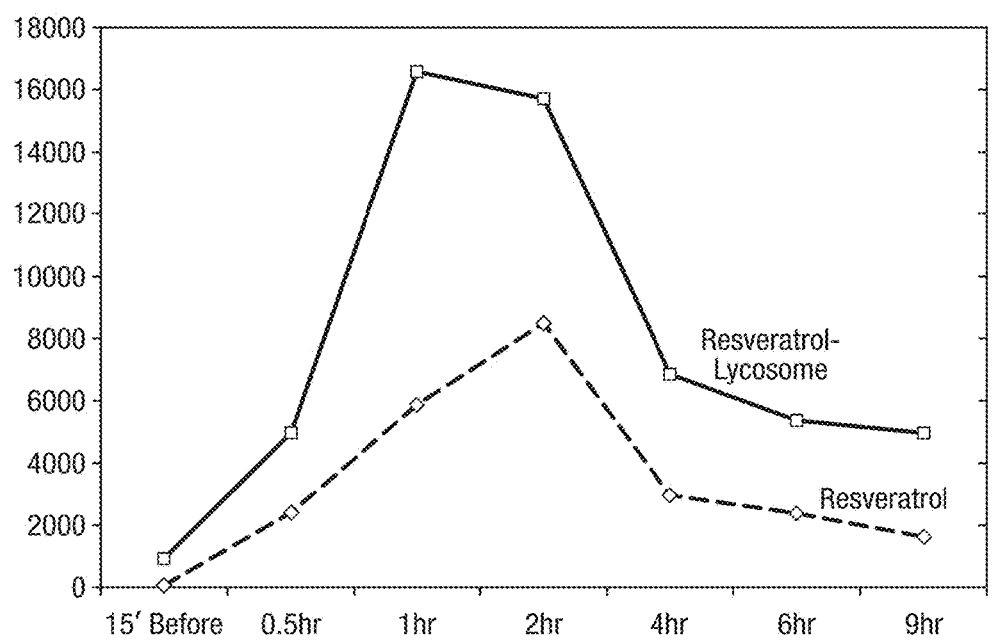
FIG. 2 shows the effect of incorporation of 100 mg resveratrol into lycosome particles on bioavailability. Data shows the combined serum concentrations of resveratrol and its metabolites in serum in ng/ml.

Table 1 shows the effect of WP and lycopene products on anti-*Chlamydia* IgG in CHD patients Table 2 shows the effect of WP and lycopene products on serum cholesterol in CHD patients.

Table 3 shows the serum concentrations of trans-resveratrol 3-sulfate in ng/ml in patients administered 120 mg resveratrol alone or in a lycopene particle.

Table 4 shows the serum concentrations of trans-resveratrol 4'-o-β-D-glucuronide in ng/ml in patients administered 120 mg resveratrol alone or in a lycopene particle.

Table 5 shows the area under the curve (AUC) for the pharmacokinetics of two trans-Resveratrol products, free form and embedded into lycopene clusters, as shown in FIG. 3.

Table 6 shows a comparison of the metabolic effect of soy-isoflavone (SI) administered with free lycopene (SI+lycopene) or incorporated into a lycopene particle (SI-lycosome).

EXPERIMENTS

1. Effect of Whey Protein on *Chlamydia*

The link between persistent *Chlamydia* infection and development of atherosclerosis has been has been established more than 25 years ago [1, 2]. Until recently a potential causative role of this infection has been occasionally questioned but remains unanswered. However, in the last year a number of publications started to shed some light on processes which may lay behind changes in lipid/cholesterol metabolism triggered by *Chlamydia* infection [3-5].

In this study, we investigated whether whey protein has anti-bacterial and in particular anti-*Chlamydia* properties.

1.1 Methods

Whey Protein 10 mg of 100% whey protein (Multipower) were dissolved in 1 ml of PBS. Two fold dilutions were prepared in RPMI and used for cell culture.

Cell Culture and Organisms

McCoy cells were cultured in 5% $CO_2$ in RPMI supplemented with 10% Fetal Bovine Serum (FBS) and 2 mM glutamine. Cells were grown in 24 well plates with round glass coverslips. Strain L2/Bu434 of *C. trachomatis* was kindly provided by Dr. P. Saikku (University of Oulu, Finland). Chlamydial strain was initially propagated in McCoy cells and purified by Renografin gradient centrifugation as described [6]. Chlamydial titers were determined by infecting McCoy cells with 10-fold dilutions of thawed stock suspension. Purified elementary bodies (EB) with known titer were suspended in sucrose-phosphate-glutamic acid buffer and used as inoculums for McCoy cells.

Cells Infection

McCoy plates were infected with *C. trachomatis* at multiplicity rate 2:1 in RPMI with 5% FBS and without cycloheximide and centrifuged for 1 hour at 1500 g at 25° C. Whey protein at concentration of 0.007-0.5 mg/ml was added to infected cells and plates were inoculated for 48 hours at 5% $CO_2$ at 37° C.

Immunofluoresence Staining

Infected McCoy monolayers grown on coverslips in 24 well plates in the presence of different concentrations of Whey protein were fixed with methanol. Permeabilized cells were stained by direct immunofluoresence using FITC— conjugated monoclonal antibody against chlamydial lipopolysaccharide (NearMedic Plus, RF). Inclusion-containing cells were visualized using Nikon Eclipse 50i microscope fluorescence microscope at X1350 magnification.

1.2 Results

Whey protein was observed to have a dose dependent effect on *Chlamydia* inclusions in McCoy cells (FIG. 1).

2. Production of Lycopene Particles

The main principle for the production of lycopene particles (Lycosomes™) is to facilitate the incorporation of the selected cargo molecules into the lycopene matrix.

This may be achieved by pre-solubilisation of lycopene and the cargo molecules in the same solvent, for example ethanol. Alternatively, the cargo molecules and lycopene may be dissolved in different solvents, for example, two different organic solvents, or an organic solvent and an oil. Preferably, the cargo molecules and lycopene are soluble either in full or in part in both solvents.

On the second step lycopene solution should be blended/mixed with the solution(s) of the product(s), under conditions which allow for incorporation the molecules of the products, or their parts, into the lycopene matrix.

Then the solvent(s) can be fully or partially evaporated which provides a residual substance in a dried, or a concentrated liquid form.

Production of lycopene particles may also be achieved by completely or partially dissolving lycopene in a solvent and spraying it over, or mixing it with cargo molecules in a dry, powdered form. The dried particles of the cargo molecules are then captured by the lycopene droplets. The lycopene solvent may then be dried out or evaporated to produce solid particles.

Alternatively, the mixture of solubilised lycopene and dried cargo molecules can stay in a form of suspension.

Techniques applied for preparation of the lycosome products in the examples described in this application are described below. For example, WP-Lycosomes were prepared using organic solvent(s) on the initial stage then vegetable oil; Resveratrol-Lycosomes and LycoStatin were prepared by separately dissolving lycopene and Simvastatin in ethanol, mixing them in the chosen ration and subsequently evaporating the solvent from the mixture, or spray-drying the mixture; IS-Lycosomes were prepared by mixing an ethanol (full or partial) solution of lycopene with granulated soy-isoflavones.

3. Preparation of Whey Protein Lycosomes

Lycopene particles incorporating whey proteins (WP-lycosomes) were produced as described in US20020107292. Briefly, 13.3 kg of whey protein isolate were dissolved in 330 l of demineralized water and the mixture stirred for 6 hours at 25-30° C. Separately, 550 g of Lycored™ oleoresin (LycoRed Corp NJ USA) comprising 6% of lycopene, was mixed in 438 l of acetone and the mixture was stirred.

The two solutions were subsequently mixed for 60 min at 30° C. The final mixture was moderately heated and the acetone was driven off at a moderate pressure. Finally, water was partially driven off at a pressure of 40-50 mbar. An aqueous solution of 200 kg of whey protein isolate and of oleoresin was obtained, which was subsequently spray dried.

Following spray drying, 186 g of soy lecithin in vegetable oil was added and mixed at 30° C. with the mass of the product.

Lycopene particles incorporating reveratrol were prepared using a spray dry method. The formulation components were prepared in absolute ethanol.

The material was prepared as follows:

5 g 99% trans-resveratrol 3.333 g Lyc-O-Mato 15% OS (i.e. 500 mg lycopene)

0.110 g lecithin

Ratio: 100 mg resveratrol: 10 mg lycopene: 2.2 mg lecithin 5 g resveratrol was dissolved in 100 ml absolute ethanol. 3.333 g Lyc-O-Mato 15% and 110 mg lecithin were dissolved in a separate volume of 100 ml absolute ethanol. The two solutions were mixed together and spray dried at 56° C. under nitrogen. The resulting powder was encapsulated as 203 mg per size 0 capsule to give a dose of 120 mg resveratrol/12 mg lycopene.

In other experiments, 20 g of 99% trans-Resveratrol was dissolved in 100 ml of 95% of ethanol, and 35 mg of tomato oleoresin (10% lycopene) was dissolved separately in 95% ethanol. Then the both solvents were mixed for 60 mins at 30° C. at then spray-dried. Lycopene particles incorporating simvastatin were prepared using an evaporation method.

180 size 0 capsules were prepared, each contained 10 mg lycopene and 20 mg simvastatin along with 106 mg lecithin.

An evaporation method was used and the resulting solid material was collected and ground in a mortar. The powder obtained was used for encapsulation. This method is comparable to rotogranulation of larger quantities of material in a commercial environment.

The production method for this 180 dose batch was as follows:

19 g lecithin 48.5 g cornflour 3.6 g simvastatin 18 g Lyconattm 10% CWD (Vitatene Ltd) (i.e. 1.8 g lycopene) Total solids: 89.1 g The 18 g Lyconat 10% CWD was dispersed in 180 ml RO H2O and made up to 1,800 ml with absolute ethanol to give a dispersion in 90% ethanol. 3.6 g simvastatin was dissolved in 90 ml ethanol, added to the lycopene dispersion in 90% ethanol and allowed to blend. 19 g lecithin was then added to the mixture and allowed to blend with the lycopene/simvastatin. The solvents were then evaporated.

The resulting solid was collected, ground to a powder and encapsulated. 1 dose contained 495 mg in a size 0 capsule. Each dose was composed of 10 mg lycopene, 106 mg lecithin, 20 mg simvastatin 269 mg cornflour, 90 mg starch from Lyconat 10% CWD In other experiments, 20 g of Simvastatin was dissolved in 100 ml of 95% of ethanol, and 7 g of lycopene from Vitatene was dissolved separately in 95% ethanol. Both solvents are mixed for 60 mins at 30° C. and then spray-dried.

Lycopene particles incorporating soy isoflavones were prepared using an evaporation method.

550 g of Lycored™ oleoresin (LycoRed Corp NJ USA) comprising 6% of lycopene, was mixed in 438 l of acetone (95% ethanol might be used as an alternative) and the solution was stirred. The lycopene solution was then mixed with soy isoflavones in a powdered form and the mixture spray dried.

In other experiments, lycopene particles incorporating soy isoflavones were produced by dissolving 550 g of Lycored™ oleoresin (LycoRed Corp NJ USA) comprising 6% of lycopene, was mixed in 438 l of ethanal and separately dissolving soy isoflavones in water.

The two solutions were subsequently mixed in the ratio of 50 g SI to 7 g or 14 g lycopene for 60 min at 30° C. The final mixture was moderately heated and the ethanol was driven off at a moderate pressure. Finally, water was partially driven off at a pressure of 40-50 mbar and the resultant solution spray dried.

4. Effects of Whey Protein Incorporated into Lycopene Particles

To verify the potential effect of WP-Lycosomes™, a clinical trial was undertaken.

20 Coronary Heart Disease (CHD) patients who were positive for anti-*Chlamydia* IgG and hypercholesterolaemia were identified. These patients were randomised in 4 groups of 5 patients, and each of them received daily either in:
 $1^{st}$ group—7 mg of lycopene supplement (in 70 mg of tomato oleoresin), or
 $2^{nd}$ group—700 mg of WP, or
 $3^{rd}$ group—mechanical mixture of 7 mg of lycopene (in 70 mg of tomato oleoresin), and 70 mg of WP, or
 $4^{th}$ group—WP-Lycosome comprising of 7 mg of lycopene (in 70 mg of tomato oleoresin) and 70 mg of WP.

Serum anti-*Chlamydia* IgG and total serum cholesterol were measured after 4 weeks.

The results show that WP itself has no ability to affect the level of *Chlamydia* infection in these patients, in terms of the specific IgG, or cholesterol concentration (Tables 1 and 2).

Lycopene on its own has some ability to reduce *Chlamydia* infection, but its effect is only observed from the $2^{nd}$ week of its administration onwards and the total sero-negativity for all patients was only achieved in the last week of the trial.

Mechanical mixing of lycopene with whey protein substantially diminished the ability of lycopene to reduce *Chlamydia* infection and 4 out of 5 patients (80%) remained sero-positive by the end of the trial (4 weeks).

Lycopene on its own was observed to have a measurable effect on serum cholesterol. After 4 weeks it reduced cholesterol by 0.7 mmol/L. Mechanical mixing of lycopene with whey protein also substantially diminished this cholesterol-lowering effect.

However, whey protein incorporated into lycopene particles, as described herein (WP-Lycosome™) displayed a profound and very rapid effect on both *Chlamydia* infection and cholesterol levels. Anti-*Chlamydia* IgG were cleared from all patients serum by the end of the $1^{st}$ week of the trial. Cholesterol levels in patients treated with WP-Lycosomes displayed a significantly deeper reduction than that produced by lycopene on its own (by 2 mmol/L).

These results show that, on top of "mild" anti-infective and cholesterol lowering properties of lycopene itself, there is a significant synergetic effect of the whey protein when it is incorporated into lycosomes.

By contrast, mechanical mixing of whey protein and lycopene was found to inactivate the latter without increasing the activity of the former.

These results show that incorporating whey protein into lycopene particles allows the anti-bacterial potential of the whey protein to be delivered to the liver.

These cell culture tests show that whey protein has a direct anti-*Chlamydia* effect. This effect has not been shown for lycopene. The effects of the whey protein are concentration dependent. There is no increase in lycopene concentration in carotenoid particles relative to lycopene itself. This indicates that the effect is due to Whey protein.

Although lycopene has been shown to reduce the symptoms of infection in vivo, this effect may be linked to its anti-oxidative and/or anti-inflammatory properties, and is generally evident after about 4 weeks. By contrast, whey protein acts much faster, and symptoms of *Chlamydia* infection, such as specific IgGs, disappear from the blood within days.

5. Effects of Resveratrol Incorporated into Lycopene Particles

To verify the potential effect of lycosome technology on Resveratrol bioavailability a pharmacokinetic study on volunteers was undertaken.

Resveratrol was incorporated into lycopene particles as described herein.

Clinical Protocol

The group of 5 volunteers comprised of 2 female and 3 male clinically healthy Caucasian persons, age between 23 and 35 years. They were asked, before commencing this experiment, to go for 3-4 days "wash-out", when consumption of any grape, wine, peanut, chocolate and other products which might contain them.

In the morning of the experiment, one hour after light breakfast, volunteers were given 1 gelatine capsule containing 100 mg of a trans-Resveratrol product, tRSV. Blood samples were taken from their median cubital or cephalic veins at the baseline point. Then, after administration of tRSV, their blood was taken again at the following time points: 30 minutes, 1 hour, 2, 3, 4, 6 and 8 hours. After the 4 hours time point, volunteers had a light lunch which did not involve consumption of any grape, wine, peanut, chocolate and other products which might contain them.

After taking blood its serum was separated, aliquoted and stored at −80° C. for further testing. The study was blinded, cross-over, and each participant was involved in testing of all three resveratrol products.

tRSV Products

Two separately manufactured batches of tRSV-Lycosome, and one batch of tRSV itself. Resveratrol for all these products was from the same batch of the same manufacturer.

5a. Study on Bioavailability of the Total Resveratrol

The results of this study are presented in the table 3 and table 4. These results demonstrate that, when resveratrol was administered in a form of lycosome, the level of two its major metabolites of, 3-sulfate and 4'-o-β-D-glucuronide, was about 2-3 fold higher than when Resveratrol was administered on its own.

A comparison of the pharmacokinetics of all main resveratrol metabolites is presented in the FIG. 2. These data show that administration of resveratrol within a lycopene particle (i.e. a lycosome) increases bioavailability relative to the same 100 mg dose of resveratrol on its own.

5b. Study on Bioavailability of Unmodified Trans-Resveratrol

A comparative pharmacokinetics of two trans-Resveratrol products, free form and embedded into lycopene clusters, is presented in the FIG. 3. A comparison of area under the curve, AUC, for two these products is presented in the Table 5. These results showed that incorporation of tRSV into lycopene was able to deliver this molecule in unmodified form, into the human blood, about 10 times more than when it was administered in free crystals.

6. Effects of Statin Incorporated into Lycopene Particles

18 CHD patients with hypercholesterolaemia were randomised in 5 equal groups:
- in $1^{st}$ group—patients received daily 1 capsule of 7 mg of lycopene supplement,
- in $2^{nd}$ group—patients received daily 1 capsule 20 mg of Simvastatin,
- in $3^{rd}$ group—patients received daily 1 capsule 40 mg of Simvastatin,
- in $4^{th}$ group—patients received daily 1 capsule 80 mg of Simvastatin,
- in $5^{th}$ group—patients received daily 1 capsule of Lycosome-Simvastatin (Lycostatin™), which was comprised of 7 mg of lycopene and 20 mg of Simvastatin.

Capsules were of the same colour and size and all ingredients for Lycostatin™ were from the same batches of the same manufacturers as for the separated products.

Figure 4C:
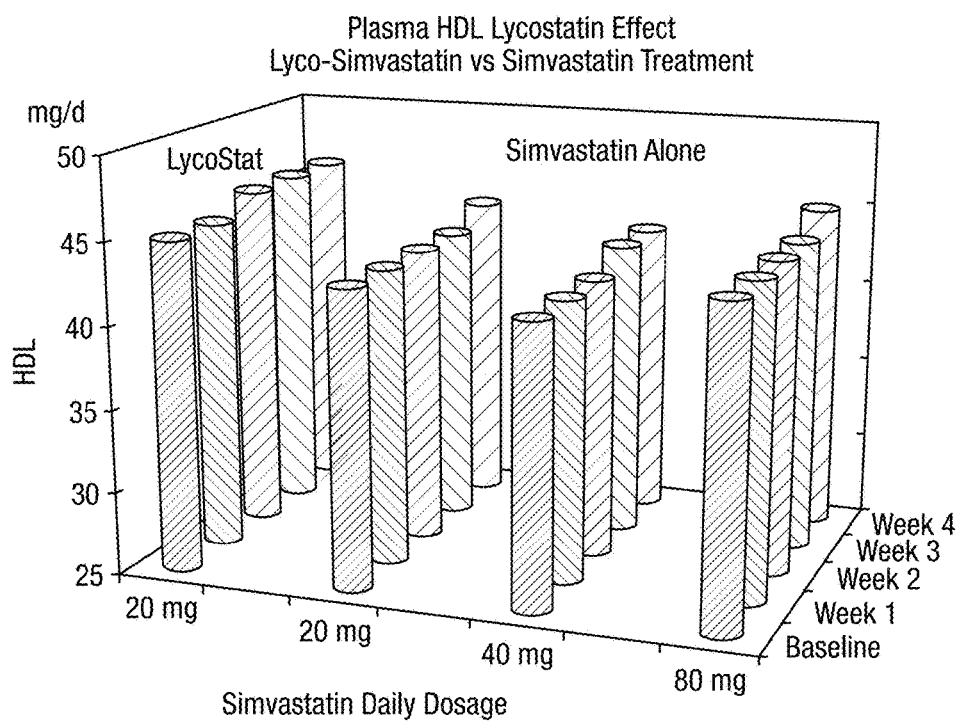

The results of this trial are presented in FIGS. 4A to 4C.

Since in the lycopene control group there were significant changes in serum concentrations of tested lipid these results were not presented in the FIGS. 4A to 4C.

At the same time all Simvastatin-contained products demonstrated significant ability to reduce total and LDL-cholesterol. There was clear dose-dependency in three groups which received free Simvastatin.

However, in the group which received 20 mg, the smallest dose of the drug, but embedded into the lycopene clusters, there were most powerful reduction in concentrations of total and LDL-cholesterol. Both the rate and the level of this reduction were more profound even than in the group which received 80 mg of free Simvastatin.

This provides indication that lycosome technology focuses drug delivery to the liver, which may potentially result in the reduction of the dose of the statin used, and consequently minimise its side effects.

7. Effects of Incorporation into Lycopene Particles of Soy Isoflavone

Soy, particularly soy isoflavones, are one of the key components of the Oriental Diet responsible for the prevention of the development of Metabolic Syndrome and Diabetes.

However, bioavailability and efficacy problems have been encountered in the extraction of isoflavones from their natural matrix and the development of dietary isoflavone supplements. Isolated isoflavones do not match the beneficial metabolic effects of the isoflavones within in a food matrix, even at the same dosages as the usual soy contained in the Oriental Diet.

One option to address low bioavailability is to increase the dose of isolated isoflavone which is administered. Increased dosages may lead to significantly increased concentrations of isoflavones in the blood and subsequently in the tissues, which may in turn, activate estrogenic hormone receptors. Although estrogenic hormone receptor activation is already used as a part of hormone-replacement therapy in post-menopausal women, activation of these receptors would not be desirable in women of other age groups or in men.

Another option is to focus the delivery of the isoflavones to the main metabolic organ (the liver) without increasing overall levels in the blood stream. Lycopene or other carotenoid compounds may be used as carriers to target the liver, which is rich with carotenoid receptors.

Soy Isoflavones were incorporated into lycopene particles (SI-Lycosomes™) and their metabolic activity and pharmacokinetics were compared with those of two other products: SI on its own and SI mechanically mixed with lycopene.

42 patients with Metabolic Syndrome, elevated total cholesterol and/or triglycerides, were randomised in 3 equal groups:
- in $1^{st}$ group—patients received daily 50 mg of SI,
- in $2^{nd}$ group—patients received daily of the mechanical mixture of 50 mg of SI and 7 mg of Lycopene, [SI+Lycopene],
- in $3^{rd}$ group—patients received SI-Lycosome™, 50 mg:7 mg of SI and Lycopene respectively as a daily dose.

3 patients in the second group and 4 in the third left the trial for low compliance reasons. Therefore only 34 patients managed to complete the trial.

Capsules used in all three groups were of the same colour and size and all ingredients for SI-Lycosomes™ were from the same batches of the same manufacturers as for the separated products.

Lipid parameters were measured and the results shown in Table 6. These results show that neither SI alone or mechanically mixed with lycopene had any significant effect on any analysed parameters of lipid metabolism in patient serum after 1 month of administration.

Figure 5:
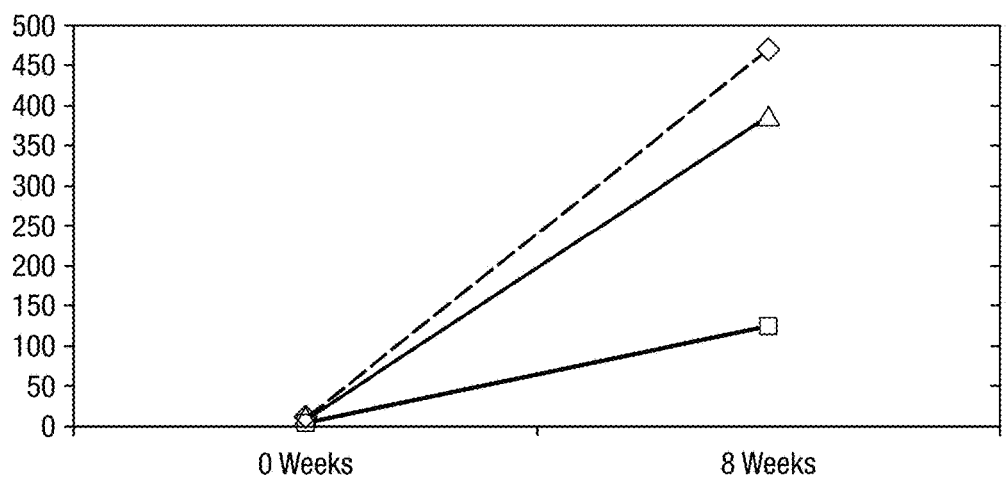
FIG. 5 shows the combined isoflavone concentrations in ng/ml in the serum of SI only patients (Δ), SI+lycopene patients (□) and SI in lycopene particles patients (◇).

Mechanical mixing of SI with lycopene resulted in the significant reduction of the absorption of the isoflavones, which was registered both in this (FIG. 5), and in additional 24 h pharmacokinetic trials (FIG. 6, 7).

However, the same dose of SI delivered in a lycopene particle has a significant lowering effect on elevated triglycerides, total cholesterol, LDL and Apo-proteins.

The observed metabolic effect of SI-Lycosome™ is unlikely to be due to the lycopene component itself because the increase in the lycopene concentration in serum of patients after 1 month of the administration of SI-Lycosome™ was about 3 times lower than in the group of patients who received the same dose of lycopene but in the mechanical mixture with SI. The increment in the former group was 150 ng/ml and in the latter 50 ng/ml (FIG. 8).

Figure 10:
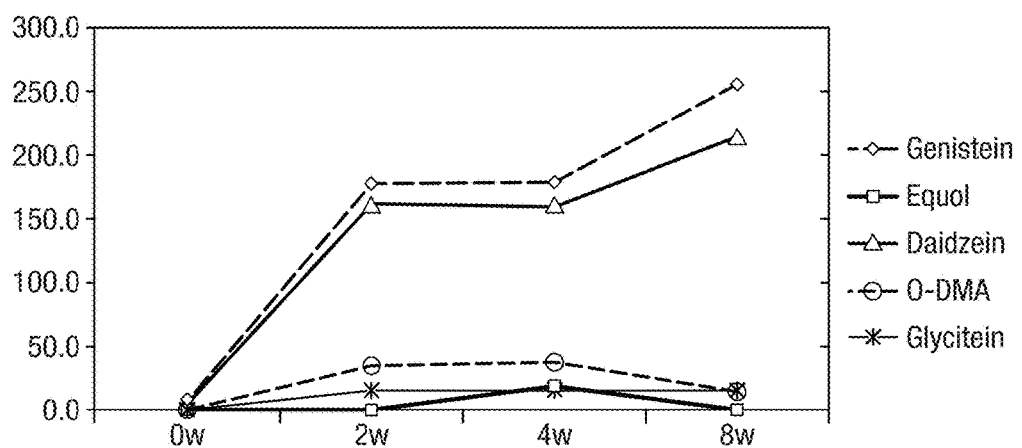
FIG. 10 shows the serum concentrations of soy isoflavones in the serum of SI in lycopene particles patients (blue).

FIGS. 9 and 10 show that incorporation of SI into lycopene particles does not create a new serum profile of isoflavones, compared with the free SI.

Therefore, results herein show that the metabolic efficacy of SI is significantly boosted by incorporation into lycopene particles without increase of SI level sin blood. This liver response is possible due to the targeting of the liver by isoflavones incorporated into the carotenoid particle.

Since carotenoids get absorbed to a significant degree via mechanical pathways, as independent physical particles and/or as a part of chylomicron, without their chemical modification, they can serve not only as a protective parcel but also as a protective currier or vehicle for the incorporated molecules or substances which could deliver them into the circulation in unmodified form.

Therefore, if some molecules or compounds are captured, in full or in part, by lycopene molecules this can provide some protection, from such GIT factors as enzymatic degradation, oxidation, stomach acidity, gut flora, etc. The outcome of this could be an increase in absorption of these vulnerable substances and their delivery to the liver in their unmodified forms, i.e. increase in their bioavailability.

REFERENCES

1. *Chlamydia* atherosclerosis lesion, discovery, diagnosis and treatment. S Shor A. Springer-Verlag. 2007
2. Chronic perivascular inoculation with Chlamydophilia pneumoniae results in plaque formation in vivo. Engelmann M G, Redl C V, Pelisek J, Barz C, Heesemann J, Nikol S. Lab Invest. 2006 May; 86(5):467-76.
3. *Chlamydia trachomatis* growth inhibition and restoration of LDL-receptor level in HepG2 cells treated with mevastatin. Bashmakov Y K, Zigangirova N A, Pashko Y P, Kapotina L N, Petyaev I M. Comp Hepatol. 2010 Jan. 28; 9:3.
4. ApoB-containing lipoproteins promote infectivity of chlamydial species in human hepatoma cell line. Yuriy K Bashmakov, Nailia A Zigangirova, Alexander L Gintzburg, Petr A Bortsov, Ivan M Petyaev World J Hepatol 2010 Feb. 27; 2(2):74-80
5. Isolation of *Chlamydia pneumoniae* from serum samples of the patients with acute coronary syndrome. Petyaev I M, Zigangirova N A, Petyaev A M, Pashko U P, Didenko L V, Morgunova E U, Bashmakov Y K. Int J Med Sci. 2010 Jun. 10; 7(4):181-90.
6. Purification and partial characterization of the major outer membrane protein of *Chlamydia trachomatis*. Galdwell H D, Kromhout J., Schachter J. Infect Immun, 1981; 31(3): 1161-1176.

TABLE 1

Effect of different Lycopene products on *Chlamydia pneumoniae* load in IgG-ELISA*

| Product | 0 w | 1 w | 2 w | 3 w | 4 w |
|---|---|---|---|---|---|
| Controls: | | | | | |
| GA Lycopene 7 mg | $0.997 \pm 0.098$ (10)** | (10) | (4) | (2) | $0.288 \pm 0.043$ (0) $p < 0.001$ |
| Whey protein 700 mg | $0.976 \pm 0.102$ (10) | (8) | (10) | (8) | $0.842 \pm 0.095$ (5) $p > 0.05$ |
| Mechanical mixture of Lycopene 7 mg + Whey protein 70 mg | $0.755 \pm 0.091$ (10) | (10) | (4) | (8) | $0.510 \pm 0.069$ (4) $p < 0.01$ |
| WP-lycosome "Delox" Lycopene 7 mg + Whey protein 70 mg | $1.047 \pm 0.136$ (10) | (0) | (0) | (0) | $0.211 \pm 0.054$ (0) $p < 0.001$ |

*ELISA reading, below 0.300-0.400 is considered to be negative
**number of sero-positive patients

TABLE 2

Cholesterol lowering effect of WP-lycosome

| | Total serum Cholesterol, in mmol/L | | | Total serum Lycopene, in ng/ml | | |
|---|---|---|---|---|---|---|
| Product | 0 w | 4 w | Δ* | 0 w | 4 w | Δ* |
| Controls: | | | | | | |
| GA Lycopene 7 mg | $5.4 \pm 0.23$ | $4.7 \pm 0.21$ | −0.7 $p < 0.05$ | $179 \pm 21$ | $295 \pm 23$ | +116 $p < 0.001$ |
| Whey protein 700 mg | $5.6 \pm 0.35$ | $5.5 \pm 0.19$ | −0.1 $P > 0.05$ | $192 \pm 18$ | $168 \pm 15$ | −24 $P > 0.05$ |
| Mechanical mixture of Lycopene 7 mg + Whey protein 70 mg | $5.2 \pm 0.32$ | $4.6 \pm 0.35$ | −0.6 $p > 0.05$ | $209 \pm 22$ | $173 \pm 18$ | −36 $p > 0.05$ |
| WP-lycosome "Delox" Lycopene 7 mg + Whey protein 70 mg | $6.2 \pm 0.36$ | $4.2 \pm 0.18$ | −2.0 $p < 0.01$ | $124 \pm 14$ | $232 \pm 17$ | +108 $p < 0.001$ |

*difference in the parameter after 4 weeks of administration

TABLE 3

Trans-resveratrol 3-sulfate in ng/ml max concentration

| ID | Resveratrol-Lycosome batch 1 120 mg | Resveratrol-Lycosome batch 2 120 mg | Resveratrol 120 mg |
|---|---|---|---|
| 1 | 1960 | 3230 | 1710 |
| 2 | 1900 | 1450 | 729 |
| 3 | 662 | 1810 | 415 |
| 4 | 2690 | 464 | 1056 |
| 5 | 824 | 2030 | 648 |
|  | 8036 | 8984 | 4558 |

TABLE 4

Trans-resveratrol 4'-o-β-D-glucuronide in ng/ml max concentration

| ID | Resveratrol-Lycosome batch 1 120 mg | Resveratrol-Lycosome batch 2 120 mg | Resveratrol 120 mg |
|---|---|---|---|
| 1 | 589 | 1000 | 289 |
| 2 | 1170 | 1130 | 73 |
| 3 | 173 | 306 | 140 |
| 4 | 891 | 266 | 361 |
| 5 | 781 | 732 | 205 |
|  | 3604 | 3434 | 1068 |

TABLE 5

AUC for 24 hours

| 100 mg trans-Resveratol | Volunteer ID 1 | Volunteer ID 2 |
|---|---|---|
| Resveratrol-Lycosome ™ 02 | 1600 | 1900 |
| Resveratrol-Lycosome ™ 03 | 1140 | 2890 |
| Crystal Resveratrol | 432 | 275 |

TABLE 6A

SI

| gender | age | TC | TG | HDL | LDL | ApoA | ApoB | AST | ALT |
|---|---|---|---|---|---|---|---|---|---|
|  |  |  |  | Before |  |  |  |  |  |
| m | 57 | 214 | 131 | 40 | 150 | 120 | 117 | 41 | 56 |
| m | 50 | 257 | 89 | 39 | 182 | 180 | 90 | 42 | 78 |
| m | 73 | 223 | 182 | 49 | 160 | 175 | 140 | 30 | 37 |
| m | 71 | 225 | 126 | 40 | 120 | 139 | 92 | 19 | 30 |
| m | 70 | 203 | 101 | 45 | 100 | 150 | 88 | 20 | 22 |
| f | 55 | 230 | 118 | 49 | 110 | 155 | 100 | 19 | 20 |
| m | 51 | 254 | 128 | 37 | 159 | 200 | 119 | 33 | 28 |
| f | 70 | 237 | 96 | 54 | 101 | 170 | 91 | 20 | 15 |
| m | 70 | 218 | 109 | 48 | 118 | 160 | 98 | 27 | 17 |
| f | 56 | 240 | 119 | 36 | 140 | 170 | 105 | 23 | 24 |
| f | 54 | 210 | 110 | 46 | 118 | 140 | 100 | 30 | 14 |
| m | 54 | 238 | 162 | 37 | 135 | 180 | 117 | 23 | 31 |
| f | 72 | 229 | 105 | 40 | 130 | 149 | 118 | 9 | 18 |
| m | 62 | 230 | 138 | 49 | 144 | 155 | 120 | 15 | 21 |
|  | 61.8 | 229 | 122 | 43.5 | 133 | 160 | 107 | 25.1 | 29.4 |

TABLE 6A-continued

SI

| gender | age | TC | TG | HDL | LDL | ApoA | ApoB | AST | ALT |
|---|---|---|---|---|---|---|---|---|---|
|  |  |  |  | 1 month after |  |  |  |  |  |
|  |  | 200 | 130 | 40 | 150 | 121 | 117 | 32 | 52 |
|  |  | 240 | 89 | 39 | 178 | 172 | 90 | 40 | 75 |
|  |  | 220 | 176 | 49 | 160 | 172 | 140 | 25 | 36 |
|  |  | 222 | 120 | 40 | 120 | 137 | 90 | 19 | 27 |
|  |  | 200 | 100 | 45 | 100 | 149 | 86 | 20 | 22 |
|  |  | 230 | 113 | 49 | 120 | 150 | 100 | 18 | 20 |
|  |  | 247 | 129 | 37 | 157 | 200 | 119 | 23 | 26 |
|  |  | 240 | 95 | 53 | 104 | 170 | 92 | 17 | 17 |
|  |  | 210 | 100 | 48 | 112 | 145 | 92 | 26 | 19 |
|  |  | 236 | 119 | 37 | 140 | 172 | 105 | 22 | 24 |
|  |  | 205 | 113 | 46 | 118 | 139 | 100 | 25 | 14 |
|  |  | 233 | 159 | 37 | 133 | 181 | 117 | 23 | 32 |
|  |  | 228 | 111 | 38 | 126 | 144 | 110 | 10 | 16 |
|  |  | 235 | 140 | 48 | 143 | 155 | 122 | 14 | 19 |
|  |  | 225 | 121 | 43.3 | 133 | 158 | 106 | 22.4 | 28.5 |

TABLE 6B

SI + Lycopene

| gender | age | TC | TG | HDL | LDL | ApoA | ApoB | AST | ALT |
|---|---|---|---|---|---|---|---|---|---|
|  |  |  |  | Before |  |  |  |  |  |
| m | 70 | 220 | 161 | 32 | 150 | 173 | 140 | 27 | 32 |
| f | 81 | 222 | 200 | 40 | 180 | 169 | 173 | 22 | 37 |
| f | 43 | 164 | 140 | 37 | 120 | 144 | 130 | 18 | 25 |
| m | 48 | 218 | 96 | 51 | 123 | 140 | 93 | 24 | 49 |
| m | 57 | 227 | 93 | 40 | 127 | 130 | 78 | 32 | 42 |
| f | 58 | 250 | 200 | 35 | 180 | 177 | 149 | 11 | 29 |
| f | 70 | 213 | 74 | 45 | 130 | 150 | 80 | 30 | 17 |
| m | 70 | 232 | 137 | 41 | 127 | 139 | 119 | 21 | 19 |
| f | 48 | 237 | 163 | 39 | 170 | 160 | 130 | 20 | 28 |
| f | 72 | 242 | 146 | 40 | 152 | 180 | 121 | 19 | 38 |
| m | 47 | 240 | 140 | 37 | 155 | 170 | 119 | 13 | 43 |
|  | 60.36 | 224 | 141 | 39.7 | 147 | 157 | 121 | 21.5 | 32.6 |
|  |  |  |  | 1 month after |  |  |  |  |  |
|  |  | 193 | 150 | 33 | 140 | 170 | 137 | 20 | 30 |
|  |  | 227 | 200 | 40 | 178 | 170 | 170 | 19 | 35 |
|  |  | 175 | 137 | 37 | 121 | 144 | 130 | 17 | 24 |
|  |  | 220 | 108 | 50 | 125 | 141 | 94 | 23 | 46 |
|  |  | 229 | 100 | 40 | 125 | 133 | 79 | 27 | 40 |
|  |  | 241 | 200 | 36 | 177 | 172 | 140 | 10 | 25 |
|  |  | 212 | 76 | 45 | 130 | 150 | 80 | 23 | 18 |
|  |  | 230 | 138 | 41 | 126 | 136 | 120 | 20 | 17 |
|  |  | 224 | 160 | 39 | 170 | 155 | 130 | 20 | 27 |
|  |  | 247 | 149 | 40 | 152 | 180 | 120 | 17 | 35 |
|  |  | 246 | 146 | 37 | 155 | 172 | 120 | 12 | 39 |
|  |  | 222 | 142 | 39.8 | 145 | 157 | 120 | 18.9 | 30.5 |

TABLE 6C

SI-Lycosome

| gender | age | TC | TG | HDL | LDL | ApoA | ApoB | AST | ALT |
|---|---|---|---|---|---|---|---|---|---|
|  |  |  |  | before |  |  |  |  |  |
| m | 68 | 219 | 187 | 47 | 195 | 193 | 170 | 16 | 33 |
| m | 55 | 200 | 175 | 38 | 181 | 155 | 201 | 37 | 47 |
| f | 70 | 200 | 163 | 58 | 195 | 180 | 159 | 22 | 37 |
| f | 51 | 224 | 173 | 64 | 186 | 170 | 190 | 18 | 19 |
| m | 63 | 209 | 208 | 48 | 205 | 199 | 185 | 19 | 17 |
| f | 66 | 210 | 196 | 51 | 148 | 173 | 167 | 34 | 31 |
| f | 73 | 231 | 184 | 58 | 197 | 190 | 150 | 27 | 40 |

TABLE 6C-continued

SI-Lycosome

| gender | age | TC | TG | HDL | LDL | ApoA | ApoB | AST | ALT |
|---|---|---|---|---|---|---|---|---|---|
| m | 55 | 221 | 167 | 47 | 300 | 220 | 170 | 100 | 110 |
| f | 46 | 201 | 163 | 40 | 215 | 152 | 193 | 30 | 29 |
|  | 60.78 | 213 | 180 | 50.1 | 202 | 181 | 176 | 33.7 | 40.3 |

1 month after

| | | | | | | | | | |
|---|---|---|---|---|---|---|---|---|---|
| | | 170 | 148 | 50 | 167 | 175 | 160 | 16 | 29 |
| | | 167 | 139 | 42 | 150 | 140 | 191 | 30 | 40 |
| | | 190 | 138 | 58 | 180 | 175 | 150 | 19 | 32 |
| | | 188 | 153 | 62 | 178 | 168 | 162 | 18 | 19 |
| | | 180 | 120 | 50 | 177 | 189 | 172 | 17 | 17 |
| | | 170 | 130 | 53 | 132 | 160 | 160 | 30 | 30 |
| | | 220 | 178 | 58 | 190 | 190 | 143 | 26 | 45 |
| | | 180 | 149 | 48 | 230 | 220 | 170 | 80 | 100 |
| | | 183 | 156 | 42 | 186 | 150 | 190 | 27 | 24 |
| | | 183 | 146 | 51.4 | 177 | 174 | 166 | 29.2 | 37.3 |

The invention claimed is:

1. A particle comprising:
   simvastatin;
   lycopene; and
   lecithin; and
   wherein the weight ratio of simvastatin to lycopene is from 2:1 to 10:1; and
   wherein the size of the particle is from 100 nm to 1 μm.

2. A method for reducing plasma LDL cholesterol in a human in need thereof, the method comprising orally administering to the human a unit dosage form comprising a therapeutically effective plurality of the particles of claim 1.

3. The method of claim 2, wherein the therapeutically effective plurality of particles comprises a total of 2 to 10 mg of lycopene.

4. The method of claim 2, wherein the therapeutically effective plurality of particles comprises a total of 7 mg of lycopene.

5. The method of claim 2, wherein the therapeutically effective plurality of particles comprises a total of 20 to 80 mg of simvastatin.

6. The method of claim 2, wherein the therapeutically effective plurality of particles comprises a total of 20 mg of simvastatin.

7. A particle comprising:
   simvastatin;
   lycopene; and
   lecithin; and
   wherein the weight ratio of simvastatin to lycopene is from 10:4 to 10:3; and
   wherein the size of the particle is from 100 nm to 1 μm.

8. The particle of claim 7, wherein the weight ratio of simvastatin to lycopene is 20:7.

9. A method for reducing plasma LDL cholesterol in a human in need thereof, the method comprising orally administering to the human a unit dosage form comprising a therapeutically effective plurality of the particles of claim 7.

10. The method of claim 9, wherein the therapeutically effective plurality of particles comprises a total of 2 to 10 mg of lycopene.

11. The method of claim 9, wherein the therapeutically effective plurality of particles comprises a total of 7 mg of lycopene.

12. The method of claim 9, wherein the therapeutically effective plurality of particles comprises a total of 20 to 80 mg of simvastatin.

13. The method of claim 9, wherein the therapeutically effective plurality of particles comprises a total of 20 mg of simvastatin.

14. The method of claim 9, wherein the therapeutically effective plurality of particles comprises a total of 7 mg of lycopene and 20 mg of simvastatin.

15. A particle comprising:
   simvastatin;
   lycopene; and
   lecithin; and
   wherein the weight ratio of simvastatin to lycopene is from 2:1 to 10:1; and
   wherein the size of the particle is from 1 nm to 100 nm.

16. A method for reducing plasma LDL cholesterol in a human in need thereof, the method comprising orally administering to the human a unit dosage form comprising a therapeutically effective plurality of the particles of claim 15.

17. The method of claim 16, wherein the therapeutically effective plurality of particles comprises a total of 2 to 10 mg of lycopene.

18. The method of claim 16, wherein the therapeutically effective plurality of particles comprises a total of 7 mg of lycopene.

19. The method of claim 16, wherein the therapeutically effective plurality of particles comprises a total of 20 to 80 mg of simvastatin.

20. The method of claim 16, wherein the therapeutically effective plurality of particles comprises a total of 20 mg of simvastatin.

* * * * *